United States Patent [19]

Stafford et al.

[11] Patent Number: 5,268,275
[45] Date of Patent: Dec. 7, 1993

[54] VITAMIN K-DEPENDENT CARBOXYLASE

[75] Inventors: Darrel W. Stafford; Sheue-Mei Wu, both of Carrboro, N.C.

[73] Assignee: The University of North Carolina at Chapel Hill, Chapel Hill, N.C.

[21] Appl. No.: 756,250

[22] Filed: Sep. 9, 1991

Related U.S. Application Data

[63] Continuation-in-part of Ser. No. 697,427, May 8, 1991, abandoned.

[51] Int. Cl.$^5$ .............. C12P 21/00; C12N 9/88; C12N 1/00; C12N 5/00; C12N 15/60; C12N 15/67; C07H 21/04

[52] U.S. Cl. .................. 435/691; 435/69.6; 435/172.1; 435/172.3; 435/240.2; 435/252.3; 435/320.1; 536/23.2; 935/10; 935/34; 935/49

[58] Field of Search .......... 435/69.1, 69.6, 110, 435/232, 172.1, 240.2, 320.1, 252.3, 240.1; 536/27, 23.2; 935/10, 34, 49

[56] References Cited

U.S. PATENT DOCUMENTS

4,912,038 3/1990 Schilling et al. ............ 435/172.3
5,100,798 3/1992 Vermeer et al. ............ 435/232

FOREIGN PATENT DOCUMENTS

87/00002 1/1987 PCT Int'l Appl.
WO88/03926 6/1988 PCT Int'l Appl.
WO91/01372 2/1991 PCT Int'l Appl.

OTHER PUBLICATIONS

Wu et al. (1991, Mar. 15) Proc. Natl. Acad. Sci. USA 88(6):2236–2240.
Hubbard et al. (1989, Sep.) Proc. Natl. Acad. Sci. USA 86:6893–6897.
Van Haarlem et al. (1987) Biochem. J. 245:251–255.
J. Girardot, *The Journal of Biological Chemistry*, 257, No. 24, 15008–15011 (1982).
M. Harbeck et al., *Thrombosis Research* 56, 317–323 (1989).
S. Wu et al., *The Journal of Biological Chemistry* 265, No. 22, 13124–13129 (1990).
J. Suttie, *Ann. Rev. Biochem.* 54, 459–477 (1985).
S. Munro et al., *Cell* 46, 291–300 (1986).
S. Wu et al., *Science* 254, 1634–1636 (1991).
Hematology Study Section Subcommittee 2, *Summary Statement on the Grant Application of D. Stafford titled "Structure and Function of Gamma-Glutamyl Carboxylase" Appl. No.* 1 R01 HL48318-01, (1991).

*Primary Examiner*—Robert A. Wax
*Assistant Examiner*—Gabriele E. Bugaisky
*Attorney, Agent, or Firm*—Bell, Seltzer, Park & Gibson

[57] ABSTRACT

Isolated DNA encoding a vitamin K dependent carboxylase is disclosed. The carboxylase is selected from the group consisting of: (a) isolated DNA which encodes bovine or human vitamin K dependent carboxylase; (b) isolated DNA which hybridizes to isolated DNA of (a) above and which encodes a vitamin K dependent carboxylase; and (c) isolated DNA differing from the isolated DNAs of (a) and (b) above in nucleotide sequence due to the degeneracy of the genetic code, and which encodes a vitamin K dependent carboxylase. Also disclosed are vectors and host cells containing the aforesaid DNA, methods of using the same, and purified protein coded for by the aforesaid DNA.

60 Claims, 6 Drawing Sheets

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 59 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

```
Ala  Val  Phe  Leu  Asp  His  Glu  Asn  Ala  Asn  Lys  Ile  Leu  Asn  Gln  Pro
 1              5                        10                        15

Lys  Ser  Tyr  Asn  Ser  Gly  Lys  Leu  Glu  Glu  Phe  Val  Gln  Gly  Asn  Leu
              20                        25                        30

Glu  Arg  Glu  Cys  Ile  Glu  Glu  Lys  Cys  Ser  Phe  Glu  Glu  Ala  Arg  Glu
              35                        40                        45

Val  Phe  Glu  Asn  Thr  Glu  Arg  Thr  Asn  Glu  Phe
              50                        55
```

( 2 ) INFORMATION FOR SEQ ID NO:2:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Asn  Leu  Ala  Phe  Gly  Arg  Pro  Ser  Leu  Glu  Gln  Leu  Ala  Gln  Glu  Val
 1              5                        10                        15

Thr  Tyr  Ala  Asn  Leu  Arg  Pro  Phe  Glu  Pro  Ala  Gly  Glu  Pro  Ser  Pro
              20                        25                        30

Val  Asn  Thr  Asp  Ser
              35
```

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Gly Gly Pro Glu Pro Thr Pro Leu Val Gln Thr Phe
1               5                   10

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Thr Gly Glu Leu Gly Tyr Leu Asn Pro Gly Val Phe Thr Gln Ser Arg
1               5                   10                  15

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:5:

SWRTCNGTRT TNACNGG                                              17

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

AANNTNGCNT TNGGNMG                                            17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

TCNCCNNCNG GYTCRAA                                            17

( 2 ) INFORMATION FOR SEQ ID NO:8:

( i ) SEQUENCE CHARACTERISTICS:
        ( A ) LENGTH: 55 base pairs
        ( B ) TYPE: nucleic acid (C) STRANDEDNESS: single
(D) TOPOLOGY: linear (i i) MOLECULE TYPE: cDNA (x i) SEQUENCE DESCRIPTION: SEQ ID NO:8:

AAGGGTCGCA AGTTGGCATA AGTCACTTCT TGGGCCAGCT GCTCCAGGGA AGGGC    55

(2) INFORMATION FOR SEQ ID NO:9:

(i) SEQUENCE CHARACTERISTICS:
    (A) LENGTH: 204 base pairs
    (B) TYPE: nucleic acid
    (C) STRANDEDNESS: single
    (D) TOPOLOGY: linear (i i) MOLECULE TYPE: cDNA (i x) FEATURE:
    (A) NAME/KEY: CDS
    (B) LOCATION: 1..204

(x i) SEQUENCE DESCRIPTION: SEQ ID NO:9:

| GGC | GGC | CCT | GAG | CCA | ACA | CCA | CTG | GTC | CAG | ACC | TTC | CTT | AGA | CGC | CAG | 48 |
| Gly | Gly | Pro | Glu | Pro | Thr | Pro | Leu | Val | Gln | Thr | Phe | Leu | Arg | Arg | Gln |    |
| 1   |     |     |     | 5   |     |     |     |     | 10  |     |     |     |     | 15  |     |    |

| CAA | AGG | CTC | CAG | GAG | ATT | GAA | CGC | CGA | CGA | AAT | GCC | CCT | TTC | CAC | GAG | 96 |
| Gln | Arg | Leu | Gln | Glu | Ile | Glu | Arg | Arg | Arg | Asn | Ala | Pro | Phe | His | Glu |    |
|     |     |     | 20  |     |     |     |     | 25  |     |     |     |     | 30  |     |     |    |

| CGA | CTT | GTC | CGC | TTC | TTG | CTG | CGA | AAG | CTC | TTT | ATC | TTT | CGC | CGT | AGC | 144 |
| Arg | Leu | Val | Arg | Phe | Leu | Leu | Arg | Lys | Leu | Phe | Ile | Phe | Arg | Arg | Ser |     |
|     |     | 35  |     |     |     |     | 40  |     |     |     |     | 45  |     |     |     |     |

| TTT | CTC | ATG | ACT | TGT | ATC | TCA | CTT | CGA | AAT | CTG | GCA | TTT | GGC | CGC | CCT | 192 |
| Phe | Leu | Met | Thr | Cys | Ile | Ser | Leu | Arg | Asn | Leu | Ala | Phe | Gly | Arg | Pro |     |
|     | 50  |     |     |     |     | 55  |     |     |     |     | 60  |     |     |     |     |     |

| TCC | CTG | GAG | CAG |                                                                 | 204 |
| Ser | Leu | Glu | Gln |                                                                 |     |
| 65  |     |     |     |                                                                 |     |

(2) INFORMATION FOR SEQ ID NO:10:

(i) SEQUENCE CHARACTERISTICS:
    (A) LENGTH: 68 amino acids
    (B) TYPE: amino acid
    (D) TOPOLOGY: linear (i i) MOLECULE TYPE: protein (x i) SEQUENCE DESCRIPTION: SEQ ID NO:10:

Gly Gly Pro Glu Pro Thr Pro Leu Val Gln Thr Phe Leu Arg Arg Gln
1               5                   10                  15

Gln Arg Leu Gln Glu Ile Glu Arg Arg Arg Asn Ala Pro Phe His Glu
            20                  25                  30

Arg Leu Val Arg Phe Leu Leu Arg Lys Leu Phe Ile Phe Arg Arg Ser
                35                  40                  45

Phe Leu Met Thr Cys Ile Ser Leu Arg Asn Leu Ala Phe Gly Arg Pro
        50                  55                  60

Ser Leu Glu Gln
65

(2) INFORMATION FOR SEQ ID NO:11:

(i) SEQUENCE CHARACTERISTICS:
    (A) LENGTH: 36 base pairs
    (B) TYPE: nucleic acid
    (C) STRANDEDNESS: single
    (D) TOPOLOGY: linear ( i i ) MOLECULE TYPE: cDNA ( i x ) FEATURE:
    ( A ) NAME/KEY: CDS
    ( B ) LOCATION: 1..36

( x i ) SEQUENCE DESCRIPTION: SEQ ID NO:11:

```
GGA  GAG  CCG  AGT  CCT  GTA  AAC  ACA  GAT  TCT  TCT  AAT                36
Gly  Glu  Pro  Ser  Pro  Val  Asn  Thr  Asp  Ser  Ser  Asn
 1              5                        10
```

( 2 ) INFORMATION FOR SEQ ID NO:12:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Gly  Glu  Pro  Ser  Pro  Val  Asn  Thr  Asp  Ser  Ser  Asn
 1              5                        10
```

( 2 ) INFORMATION FOR SEQ ID NO:13:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..42

( x i ) SEQUENCE DESCRIPTION: SEQ ID NO:13:

```
ACC  GGT  GAA  CTG  GGC  TAC  CTC  AAC  CCT  GGG  GTA  TTC  ACA  CAG      42
Thr  Gly  Glu  Leu  Gly  Tyr  Leu  Asn  Pro  Gly  Val  Phe  Thr  Gln
 1              5                        10
```

( 2 ) INFORMATION FOR SEQ ID NO:14:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Thr  Gly  Glu  Leu  Gly  Tyr  Leu  Asn  Pro  Gly  Val  Phe  Thr  Gln
 1              5                        10
```

( 2 ) INFORMATION FOR SEQ ID NO:15:

( i ) SEQUENCE CHARACTERISTICS:
        ( A ) LENGTH: 2452 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 87..2360

( x i ) SEQUENCE DESCRIPTION: SEQ ID NO:15:

```
CGGGGCGGAG  CCTAGGGAAG  CAAATTCTCC  TGGCGGCCTC  CGTTCAGACG  CGGCAGCTGT      60
```

| | | | | | | | | | | | | | | | |
|---|---|---|---|---|---|---|---|---|---|---|---|---|---|---|---|
| GACCCACCTG | CCTCCTCCGC | AGAGCA | ATG | GCG | GTG | TCT | GCC | GGG | TCC | GCG | CGG | | | | 113 |
| | | | Met | Ala | Val | Ser | Ala | Gly | Ser | Ala | Arg | | | | |
| | | | 1 | | | | 5 | | | | | | | | |
| ACC | TCG | CCC | AGC | TCA | GAT | AAA | GTA | CAG | AAA | GAC | AAG | GCT | GAA | CTG ATC | 161 |
| Thr | Ser | Pro | Ser | Ser | Asp | Lys | Val | Gln | Lys | Asp | Lys | Ala | Glu | Leu Ile |  |
| 10 | | | | 15 | | | | 20 | | | | | | 25 | |
| TCA | GGG | CCC | AGG | CAG | GAC | AGC | CGA | ATA | GGG | AAA | CTC | TTG | GGT | TTT GAG | 209 |
| Ser | Gly | Pro | Arg | Gln | Asp | Ser | Arg | Ile | Gly | Lys | Leu | Leu | Gly | Phe Glu |  |
| | | | | 30 | | | | | 35 | | | | | 40 | |
| TGG | ACA | GAT | TTG | TCC | AGT | TGG | CGG | AGG | CTG | GTG | ACC | CTG | CTG | AAT CGA | 257 |
| Trp | Thr | Asp | Leu | Ser | Ser | Trp | Arg | Arg | Leu | Val | Thr | Leu | Leu | Asn Arg |  |
| | | | | 45 | | | | | 50 | | | | | 55 | |
| CCA | ACG | GAC | CCT | GCA | AGC | TTA | GCT | GTC | TTT | CGT | TTT | CTT | TTT | GGG TTC | 305 |
| Pro | Thr | Asp | Pro | Ala | Ser | Leu | Ala | Val | Phe | Arg | Phe | Leu | Phe | Gly Phe |  |
| | | | 60 | | | | | 65 | | | | | 70 | | |
| TTG | ATG | GTG | CTA | GAC | ATT | CCC | CAG | GAG | CGG | GGG | CTC | AGC | TCT | CTG GAC | 353 |
| Leu | Met | Val | Leu | Asp | Ile | Pro | Gln | Glu | Arg | Gly | Leu | Ser | Ser | Leu Asp |  |
| | 75 | | | | | 80 | | | | | 85 | | | | |
| CGG | AAA | TAC | CTT | GAT | GGG | CTG | GAT | GTG | TGC | CGC | TTC | CCC | TTG | CTG GAT | 401 |
| Arg | Lys | Tyr | Leu | Asp | Gly | Leu | Asp | Val | Cys | Arg | Phe | Pro | Leu | Leu Asp |  |
| 90 | | | | | 95 | | | | | 100 | | | | | 105 |
| GCC | CTA | CGC | CCA | CTG | CCA | CTT | GAC | TGG | ATG | TAT | CTT | GTC | TAC | ACC ATC | 449 |
| Ala | Leu | Arg | Pro | Leu | Pro | Leu | Asp | Trp | Met | Tyr | Leu | Val | Tyr | Thr Ile |  |
| | | | | 110 | | | | | 115 | | | | | 120 | |
| ATG | TTT | CTG | GGG | GCA | CTG | GGC | ATG | ATG | CTG | GGC | CTG | TGC | TAC | CGG ATA | 497 |
| Met | Phe | Leu | Gly | Ala | Leu | Gly | Met | Met | Leu | Gly | Leu | Cys | Tyr | Arg Ile |  |
| | | | | 125 | | | | | 130 | | | | | 135 | |
| AGC | TGT | GTG | TTA | TTC | CTG | CTG | CCA | TAC | TGG | TAT | GTG | TTT | CTC | CTG GAC | 545 |
| Ser | Cys | Val | Leu | Phe | Leu | Leu | Pro | Tyr | Trp | Tyr | Val | Phe | Leu | Leu Asp |  |
| | | 140 | | | | | 145 | | | | | 150 | | | |
| AAG | ACA | TCA | TGG | AAC | AAC | CAC | TCC | TAT | CTG | TAT | GGG | TTG | TTG | GCC TTT | 593 |
| Lys | Thr | Ser | Trp | Asn | Asn | His | Ser | Tyr | Leu | Tyr | Gly | Leu | Leu | Ala Phe |  |
| | | 155 | | | | | 160 | | | | | 165 | | | |
| CAG | CTA | ACA | TTC | ATG | GAT | GCA | AAC | CAC | TAC | TGG | TCT | GTG | GAC | GGT CTG | 641 |
| Gln | Leu | Thr | Phe | Met | Asp | Ala | Asn | His | Tyr | Trp | Ser | Val | Asp | Gly Leu |  |
| 170 | | | | | 175 | | | | | 180 | | | | | 185 |
| CTG | AAT | GCC | CAT | AGG | AGG | AAT | GCC | CAC | GTG | CCC | CTT | TGG | AAC | TAT GCA | 689 |
| Leu | Asn | Ala | His | Arg | Arg | Asn | Ala | His | Val | Pro | Leu | Trp | Asn | Tyr Ala |  |
| | | | | 190 | | | | | 195 | | | | | 200 | |
| GTG | CTC | CGT | GGC | CAG | ATC | TTC | ATT | GTG | TAC | TTC | ATT | GCG | GGT | GTG AAA | 737 |
| Val | Leu | Arg | Gly | Gln | Ile | Phe | Ile | Val | Tyr | Phe | Ile | Ala | Gly | Val Lys |  |
| | | | | 205 | | | | | 210 | | | | | 215 | |
| AAG | CTG | GAT | GCA | GAC | TGG | GTT | GAA | GGC | TAT | TCC | ATG | GAA | TAT | TTG TCC | 785 |
| Lys | Leu | Asp | Ala | Asp | Trp | Val | Glu | Gly | Tyr | Ser | Met | Glu | Tyr | Leu Ser |  |
| | | 220 | | | | | 225 | | | | | 230 | | | |
| CGG | CAC | TGG | CTC | TTC | AGT | CCC | TTC | AAA | CTG | CTG | TTG | TCT | GAG | GAG CTG | 833 |
| Arg | His | Trp | Leu | Phe | Ser | Pro | Phe | Lys | Leu | Leu | Leu | Ser | Glu | Glu Leu |  |
| | 235 | | | | | 240 | | | | | 245 | | | | |
| ACT | AGC | CTG | CTG | GTC | GTG | CAC | TGG | GGT | GGG | CTG | CTG | CTT | GAC | CTC TCA | 881 |
| Thr | Ser | Leu | Leu | Val | Val | His | Trp | Gly | Gly | Leu | Leu | Leu | Asp | Leu Ser |  |
| 250 | | | | | 255 | | | | | 260 | | | | | 265 |
| GCT | GGT | TTC | CTG | CTC | TTT | TTT | GAT | GTC | TCA | AGA | TCC | ATT | GGC | CTG TTC | 929 |
| Ala | Gly | Phe | Leu | Leu | Phe | Phe | Asp | Val | Ser | Arg | Ser | Ile | Gly | Leu Phe |  |
| | | | | 270 | | | | | 275 | | | | | 280 | |
| TTT | GTG | TCC | TAC | TTC | CAC | TGC | ATG | AAT | TCC | CAG | CTT | TTC | AGC | ATT GGT | 977 |
| Phe | Val | Ser | Tyr | Phe | His | Cys | Met | Asn | Ser | Gln | Leu | Phe | Ser | Ile Gly |  |
| | | | 285 | | | | | 290 | | | | | 295 | | |
| ATG | TTC | TCC | TAC | GTC | ATG | CTG | GCC | AGC | AGC | CCT | CTC | TTC | TGC | TCC CCT | 1025 |
| Met | Phe | Ser | Tyr | Val | Met | Leu | Ala | Ser | Ser | Pro | Leu | Phe | Cys | Ser Pro |  |
| | | 300 | | | | | | 305 | | | | | 310 | | |
| GAG | TGG | CCT | CGG | AAG | CTG | GTG | TCC | TAC | TGC | CCC | CAA | AGG | TTG | CAA CAA | 1073 |

-continued

| Glu | Trp | Pro | Arg | Lys | Leu | Val | Ser | Tyr | Cys | Pro | Gln | Arg | Leu | Gln | Gln | |
|-----|-----|-----|-----|-----|-----|-----|-----|-----|-----|-----|-----|-----|-----|-----|-----|---|
|     | 315 |     |     |     | 320 |     |     |     |     | 325 |     |     |     |     |     |   |

| CTG | TTG | CCC | CTC | AAG | GCA | GCC | CCT | CAG | CCC | AGT | GTT | TCC | TGT | GTG | TAT | 1121 |
|-----|-----|-----|-----|-----|-----|-----|-----|-----|-----|-----|-----|-----|-----|-----|-----|------|
| Leu | Leu | Pro | Leu | Lys | Ala | Ala | Pro | Gln | Pro | Ser | Val | Ser | Cys | Val | Tyr |      |
| 330 |     |     |     |     | 335 |     |     |     | 340 |     |     |     |     |     | 345 |      |

| AAG | AGG | AGC | CGG | GGC | AAA | AGT | GGC | CAG | AAG | CCA | GGG | CTG | CGC | CAT | CAG | 1169 |
|-----|-----|-----|-----|-----|-----|-----|-----|-----|-----|-----|-----|-----|-----|-----|-----|------|
| Lys | Arg | Ser | Arg | Gly | Lys | Ser | Gly | Gln | Lys | Pro | Gly | Leu | Arg | His | Gln |      |
|     |     |     |     | 350 |     |     |     |     | 355 |     |     |     |     | 360 |     |      |

| CTG | GGA | GCT | GCC | TTC | ACC | CTG | CTC | TAC | CTC | CTG | GAG | CAG | CTA | TTC | CTG | 1217 |
|-----|-----|-----|-----|-----|-----|-----|-----|-----|-----|-----|-----|-----|-----|-----|-----|------|
| Leu | Gly | Ala | Ala | Phe | Thr | Leu | Leu | Tyr | Leu | Leu | Glu | Gln | Leu | Phe | Leu |      |
|     |     |     | 365 |     |     |     |     | 370 |     |     |     |     | 375 |     |     |      |

| CCC | TAT | TCT | CAT | TTT | CTC | ACC | CAG | GGC | TAT | AAC | AAC | TGG | ACA | AAT | GGG | 1265 |
|-----|-----|-----|-----|-----|-----|-----|-----|-----|-----|-----|-----|-----|-----|-----|-----|------|
| Pro | Tyr | Ser | His | Phe | Leu | Thr | Gln | Gly | Tyr | Asn | Asn | Trp | Thr | Asn | Gly |      |
|     |     | 380 |     |     |     |     | 385 |     |     |     |     | 390 |     |     |     |      |

| CTG | TAT | GGC | TAT | TCC | TGG | GAC | ATG | ATG | GTG | CAC | TCC | CGT | TCC | CAC | CAG | 1313 |
|-----|-----|-----|-----|-----|-----|-----|-----|-----|-----|-----|-----|-----|-----|-----|-----|------|
| Leu | Tyr | Gly | Tyr | Ser | Trp | Asp | Met | Met | Val | His | Ser | Arg | Ser | His | Gln |      |
|     | 395 |     |     |     |     | 400 |     |     |     |     | 405 |     |     |     |     |      |

| CAC | GTG | AAG | ATC | ACC | TAC | CGT | GAT | GGC | CGC | ACT | GGC | GAA | CTG | GGC | TAC | 1361 |
|-----|-----|-----|-----|-----|-----|-----|-----|-----|-----|-----|-----|-----|-----|-----|-----|------|
| His | Val | Lys | Ile | Thr | Tyr | Arg | Asp | Gly | Arg | Thr | Gly | Glu | Leu | Gly | Tyr |      |
| 410 |     |     |     |     | 415 |     |     |     |     | 420 |     |     |     |     | 425 |      |

| CTT | AAC | CCT | GGG | GTA | TTT | ACA | CAG | AGT | CGG | CGA | TGG | AAG | GAT | CAT | GCA | 1409 |
|-----|-----|-----|-----|-----|-----|-----|-----|-----|-----|-----|-----|-----|-----|-----|-----|------|
| Leu | Asn | Pro | Gly | Val | Phe | Thr | Gln | Ser | Arg | Arg | Trp | Lys | Asp | His | Ala |      |
|     |     |     | 430 |     |     |     |     | 435 |     |     |     |     | 440 |     |     |      |

| GAC | ATG | CTG | AAG | CAA | TAT | GCC | ACT | TGC | CTG | AGC | CGC | CTG | CTT | CCC | AAG | 1457 |
|-----|-----|-----|-----|-----|-----|-----|-----|-----|-----|-----|-----|-----|-----|-----|-----|------|
| Asp | Met | Leu | Lys | Gln | Tyr | Ala | Thr | Cys | Leu | Ser | Arg | Leu | Leu | Pro | Lys |      |
|     |     |     | 445 |     |     |     |     | 450 |     |     |     |     | 455 |     |     |      |

| TAT | AAT | GTC | ACT | GAG | CCC | CAG | ATC | TAC | TTT | GAT | ATT | TGG | GTC | TCC | ATC | 1505 |
|-----|-----|-----|-----|-----|-----|-----|-----|-----|-----|-----|-----|-----|-----|-----|-----|------|
| Tyr | Asn | Val | Thr | Glu | Pro | Gln | Ile | Tyr | Phe | Asp | Ile | Trp | Val | Ser | Ile |      |
|     |     | 460 |     |     |     |     | 465 |     |     |     |     | 470 |     |     |     |      |

| AAT | GAC | CGC | TTC | CAG | CAG | AGG | ATT | TTT | GAC | CCT | CGT | GTG | GAC | ATC | GTG | 1553 |
|-----|-----|-----|-----|-----|-----|-----|-----|-----|-----|-----|-----|-----|-----|-----|-----|------|
| Asn | Asp | Arg | Phe | Gln | Gln | Arg | Ile | Phe | Asp | Pro | Arg | Val | Asp | Ile | Val |      |
|     | 475 |     |     |     |     | 480 |     |     |     |     | 485 |     |     |     |     |      |

| CAG | GCC | GCT | TGG | TCA | CCC | TTT | CAG | CGC | ACA | TCC | TGG | GTG | CAA | CCA | CTC | 1601 |
|-----|-----|-----|-----|-----|-----|-----|-----|-----|-----|-----|-----|-----|-----|-----|-----|------|
| Gln | Ala | Ala | Trp | Ser | Pro | Phe | Gln | Arg | Thr | Ser | Trp | Val | Gln | Pro | Leu |      |
| 490 |     |     |     |     | 495 |     |     |     |     | 500 |     |     |     |     | 505 |      |

| TTG | ATG | GAC | CTG | TCT | CCC | TGG | AGG | GCC | AAG | TTA | CAG | GAA | ATC | AAG | AGC | 1649 |
|-----|-----|-----|-----|-----|-----|-----|-----|-----|-----|-----|-----|-----|-----|-----|-----|------|
| Leu | Met | Asp | Leu | Ser | Pro | Trp | Arg | Ala | Lys | Leu | Gln | Glu | Ile | Lys | Ser |      |
|     |     |     |     | 510 |     |     |     |     | 515 |     |     |     |     | 520 |     |      |

| AGC | CTA | GAC | AAC | CAC | ACT | GAG | GTG | GTC | TTC | ATT | GCA | GAT | TTC | CCT | GGA | 1697 |
|-----|-----|-----|-----|-----|-----|-----|-----|-----|-----|-----|-----|-----|-----|-----|-----|------|
| Ser | Leu | Asp | Asn | His | Thr | Glu | Val | Val | Phe | Ile | Ala | Asp | Phe | Pro | Gly |      |
|     |     |     |     | 525 |     |     |     | 530 |     |     |     |     | 535 |     |     |      |

| CTG | CAC | TTG | GAG | AAT | TTT | GTG | AGT | GAA | GAC | CTG | GGC | AAC | ACT | AGC | ATC | 1745 |
|-----|-----|-----|-----|-----|-----|-----|-----|-----|-----|-----|-----|-----|-----|-----|-----|------|
| Leu | His | Leu | Glu | Asn | Phe | Val | Ser | Glu | Asp | Leu | Gly | Asn | Thr | Ser | Ile |      |
|     |     | 540 |     |     |     |     | 545 |     |     |     |     | 550 |     |     |     |      |

| CAG | CTG | CTG | CAG | GGG | GAA | GTG | ACT | GTG | GAG | CTT | GTG | GCA | GAA | CAG | AAG | 1793 |
|-----|-----|-----|-----|-----|-----|-----|-----|-----|-----|-----|-----|-----|-----|-----|-----|------|
| Gln | Leu | Leu | Gln | Gly | Glu | Val | Thr | Val | Glu | Leu | Val | Ala | Glu | Gln | Lys |      |
| 555 |     |     |     |     | 560 |     |     |     |     | 565 |     |     |     |     |     |      |

| AAC | CAG | ACT | CTT | CGA | GAG | GGA | GAA | AAA | ATG | CAG | TTG | CCT | GCT | GGT | GAG | 1841 |
|-----|-----|-----|-----|-----|-----|-----|-----|-----|-----|-----|-----|-----|-----|-----|-----|------|
| Asn | Gln | Thr | Leu | Arg | Glu | Gly | Glu | Lys | Met | Gln | Leu | Pro | Ala | Gly | Glu |      |
| 570 |     |     |     |     | 575 |     |     |     |     | 580 |     |     |     |     | 585 |      |

| TAC | CAT | AAG | GTG | TAT | ACG | ACA | TCA | CCT | AGC | CCT | TCT | TGC | TAC | ATG | TAC | 1889 |
|-----|-----|-----|-----|-----|-----|-----|-----|-----|-----|-----|-----|-----|-----|-----|-----|------|
| Tyr | His | Lys | Val | Tyr | Thr | Thr | Ser | Pro | Ser | Pro | Ser | Cys | Tyr | Met | Tyr |      |
|     |     |     |     | 590 |     |     |     |     | 595 |     |     |     |     | 600 |     |      |

| GTC | TAT | GTC | AAC | ACT | ACA | GAG | CTT | GCA | CTG | GAG | CAA | GAC | CTG | GCA | TAT | 1937 |
|-----|-----|-----|-----|-----|-----|-----|-----|-----|-----|-----|-----|-----|-----|-----|-----|------|
| Val | Tyr | Val | Asn | Thr | Thr | Glu | Leu | Ala | Leu | Glu | Gln | Asp | Leu | Ala | Tyr |      |
|     |     |     | 605 |     |     |     |     | 610 |     |     |     |     | 615 |     |     |      |

| CTG | CAA | GAA | TTA | AAG | GAA | AAG | GTG | GAG | AAT | GGA | AGT | GAA | ACA | GGG | CCT | 1985 |
|-----|-----|-----|-----|-----|-----|-----|-----|-----|-----|-----|-----|-----|-----|-----|-----|------|
| Leu | Gln | Glu | Leu | Lys | Glu | Lys | Val | Glu | Asn | Gly | Ser | Glu | Thr | Gly | Pro |      |
|     | 620 |     |     |     |     | 625 |     |     |     |     | 630 |     |     |     |     |      |

| CTA | CCC | CCA | GAG | CTG | CAG | CCT | CTG | TTG | GAA | GGG | GAA | GTA | AAA | GGG | GGC | 2033 |
|-----|-----|-----|-----|-----|-----|-----|-----|-----|-----|-----|-----|-----|-----|-----|-----|------|
| Leu | Pro | Pro | Glu | Leu | Gln | Pro | Leu | Leu | Glu | Gly | Glu | Val | Lys | Gly | Gly |      |
|     | 635 |     |     |     | 640 |     |     |     |     | 645 |     |     |     |     |     |      |

| | | | | | | | | | | | | | | | | |
|---|---|---|---|---|---|---|---|---|---|---|---|---|---|---|---|---|
| CCT | GAG | CCA | ACA | CCT | CTG | GTT | CAG | ACC | TTT | CTT | AGA | CGC | CAA | CAA | AGG | 2081 |
| Pro | Glu | Pro | Thr | Pro | Leu | Val | Gln | Thr | Phe | Leu | Arg | Arg | Gln | Gln | Arg | |
| 650 | | | | 655 | | | | | 660 | | | | | | 665 | |
| CTC | CAG | GAG | ATT | GAA | CGC | CGG | CGA | AAT | ACT | CCT | TTC | CAT | GAG | CGA | TTC | 2129 |
| Leu | Gln | Glu | Ile | Glu | Arg | Arg | Arg | Asn | Thr | Pro | Phe | His | Glu | Arg | Phe | |
| | | | | 670 | | | | | 675 | | | | | 680 | | |
| TTC | CGC | TTC | TTG | TTG | CGA | AAG | CTC | TAT | GTC | TTT | CGC | CGC | AGC | TTC | CTG | 2177 |
| Phe | Arg | Phe | Leu | Leu | Arg | Lys | Leu | Tyr | Val | Phe | Arg | Arg | Ser | Phe | Leu | |
| | | | | 685 | | | | | 690 | | | | | 695 | | |
| ATG | ACT | TGT | ATC | TCA | CTT | CGA | AAT | CTG | ATA | TTA | GGC | CGT | CCT | TCC | CTG | 2225 |
| Met | Thr | Cys | Ile | Ser | Leu | Arg | Asn | Leu | Ile | Leu | Gly | Arg | Pro | Ser | Leu | |
| | | | | 700 | | | | | 705 | | | | | 710 | | |
| GAG | CAG | CTG | GCC | CAG | GAG | GTG | ACT | TAT | GCA | AAC | TTG | AGA | CCC | TTT | GAG | 2273 |
| Glu | Gln | Leu | Ala | Gln | Glu | Val | Thr | Tyr | Ala | Asn | Leu | Arg | Pro | Phe | Glu | |
| | | | | 715 | | | | | 720 | | | | | 725 | | |
| GCA | GTT | GGA | GAA | CTG | AAT | CCC | TCA | AAC | ACG | GAT | TCT | TCA | CAT | TCT | AAT | 2321 |
| Ala | Val | Gly | Glu | Leu | Asn | Pro | Ser | Asn | Thr | Asp | Ser | Ser | His | Ser | Asn | |
| 730 | | | | | 735 | | | | | 740 | | | | | 745 | |
| CCT | CCT | GAG | TCA | AAT | CCT | GAT | CCT | GTC | CAC | TCA | GAG | TTC | TGAAGGGGC | | | 2370 |
| Pro | Pro | Glu | Ser | Asn | Pro | Asp | Pro | Val | His | Ser | Glu | Phe | | | | |
| | | | | 750 | | | | | 755 | | | | | | | |

CAGATGTTGG GTGCAGATGT AGAAGCAGCC AGTCACAGAC CCATTCTATG CAATGGACAT    2430

TTATTTGAAA AAAAAAAAAA AA    2452

( 2 ) INFORMATION FOR SEQ ID NO:16:

( i ) SEQUENCE CHARACTERISTICS:
        ( A ) LENGTH: 758 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| | | | | | | | | | | | | | | |
|---|---|---|---|---|---|---|---|---|---|---|---|---|---|---|
| Met | Ala | Val | Ser | Ala | Gly | Ser | Ala | Arg | Thr | Ser | Pro | Ser | Ser | Asp | Lys |
| 1 | | | | 5 | | | | | 10 | | | | | 15 | |
| Val | Gln | Lys | Asp | Lys | Ala | Glu | Leu | Ile | Ser | Gly | Pro | Arg | Gln | Asp | Ser |
| | | | 20 | | | | | 25 | | | | | 30 | | |
| Arg | Ile | Gly | Lys | Leu | Leu | Gly | Phe | Glu | Trp | Thr | Asp | Leu | Ser | Ser | Trp |
| | | | 35 | | | | | 40 | | | | | 45 | | |
| Arg | Arg | Leu | Val | Thr | Leu | Leu | Asn | Arg | Pro | Thr | Asp | Pro | Ala | Ser | Leu |
| | 50 | | | | | 55 | | | | | 60 | | | | |
| Ala | Val | Phe | Arg | Phe | Leu | Phe | Gly | Phe | Leu | Met | Val | Leu | Asp | Ile | Pro |
| 65 | | | | | 70 | | | | | 75 | | | | | 80 |
| Gln | Glu | Arg | Gly | Leu | Ser | Ser | Leu | Asp | Arg | Lys | Tyr | Leu | Asp | Gly | Leu |
| | | | | 85 | | | | | 90 | | | | | 95 | |
| Asp | Val | Cys | Arg | Phe | Pro | Leu | Leu | Asp | Ala | Leu | Arg | Pro | Leu | Pro | Leu |
| | | | 100 | | | | | 105 | | | | | 110 | | |
| Asp | Trp | Met | Tyr | Leu | Val | Tyr | Thr | Ile | Met | Phe | Leu | Gly | Ala | Leu | Gly |
| | | | 115 | | | | | 120 | | | | | 125 | | |
| Met | Met | Leu | Gly | Leu | Cys | Tyr | Arg | Ile | Ser | Cys | Val | Leu | Phe | Leu | Leu |
| | 130 | | | | | 135 | | | | | 140 | | | | |
| Pro | Tyr | Trp | Tyr | Val | Phe | Leu | Leu | Asp | Lys | Thr | Ser | Trp | Asn | Asn | His |
| 145 | | | | | 150 | | | | | 155 | | | | | 160 |
| Ser | Tyr | Leu | Tyr | Gly | Leu | Leu | Ala | Phe | Gln | Leu | Thr | Phe | Met | Asp | Ala |
| | | | | 165 | | | | | 170 | | | | | 175 | |
| Asn | His | Tyr | Trp | Ser | Val | Asp | Gly | Leu | Leu | Asn | Ala | His | Arg | Arg | Asn |
| | | | 180 | | | | | 185 | | | | | 190 | | |
| Ala | His | Val | Pro | Leu | Trp | Asn | Tyr | Ala | Val | Leu | Arg | Gly | Gln | Ile | Phe |

-continued

```
              195                         200                         205
Ile  Val  Tyr  Phe  Ile  Ala  Gly  Val  Lys  Lys  Leu  Asp  Ala  Asp  Trp  Val
     210                      215                     220

Glu  Gly  Tyr  Ser  Met  Glu  Tyr  Leu  Ser  Arg  His  Trp  Leu  Phe  Ser  Pro
225                      230                     235                          240

Phe  Lys  Leu  Leu  Leu  Ser  Glu  Glu  Leu  Thr  Ser  Leu  Leu  Val  Val  His
                    245                     250                     255

Trp  Gly  Gly  Leu  Leu  Leu  Asp  Leu  Ser  Ala  Gly  Phe  Leu  Leu  Phe  Phe
               260                     265                     270

Asp  Val  Ser  Arg  Ser  Ile  Gly  Leu  Phe  Phe  Val  Ser  Tyr  Phe  His  Cys
          275                     280                     285

Met  Asn  Ser  Gln  Leu  Phe  Ser  Ile  Gly  Met  Phe  Ser  Tyr  Val  Met  Leu
          290                     295                     300

Ala  Ser  Ser  Pro  Leu  Phe  Cys  Ser  Pro  Glu  Trp  Pro  Arg  Lys  Leu  Val
305                      310                     315                          320

Ser  Tyr  Cys  Pro  Gln  Arg  Leu  Gln  Gln  Leu  Pro  Leu  Lys  Ala  Ala
                    325                     330                     335

Pro  Gln  Pro  Ser  Val  Ser  Cys  Val  Tyr  Lys  Arg  Ser  Arg  Gly  Lys  Ser
               340                     345                     350

Gly  Gln  Lys  Pro  Gly  Leu  Arg  His  Gln  Leu  Gly  Ala  Ala  Phe  Thr  Leu
          355                     360                     365

Leu  Tyr  Leu  Leu  Glu  Gln  Leu  Phe  Leu  Pro  Tyr  Ser  His  Phe  Leu  Thr
     370                     375                     380

Gln  Gly  Tyr  Asn  Asn  Trp  Thr  Asn  Gly  Leu  Tyr  Gly  Tyr  Ser  Trp  Asp
385                      390                     395                          400

Met  Met  Val  His  Ser  Arg  Ser  His  Gln  His  Val  Lys  Ile  Thr  Tyr  Arg
                    405                     410                     415

Asp  Gly  Arg  Thr  Gly  Glu  Leu  Gly  Tyr  Leu  Asn  Pro  Gly  Val  Phe  Thr
               420                     425                     430

Gln  Ser  Arg  Arg  Trp  Lys  Asp  His  Ala  Asp  Met  Leu  Lys  Gln  Tyr  Ala
          435                     440                     445

Thr  Cys  Leu  Ser  Arg  Leu  Leu  Pro  Lys  Tyr  Asn  Val  Thr  Glu  Pro  Gln
     450                     455                     460

Ile  Tyr  Phe  Asp  Ile  Trp  Val  Ser  Ile  Asn  Asp  Arg  Phe  Gln  Gln  Arg
465                      470                     475                          480

Ile  Phe  Asp  Pro  Arg  Val  Asp  Ile  Val  Gln  Ala  Ala  Trp  Ser  Pro  Phe
                    485                     490                     495

Gln  Arg  Thr  Ser  Trp  Val  Gln  Pro  Leu  Leu  Met  Asp  Leu  Ser  Pro  Trp
               500                     505                     510

Arg  Ala  Lys  Leu  Gln  Glu  Ile  Lys  Ser  Ser  Leu  Asp  Asn  His  Thr  Glu
          515                     520                     525

Val  Val  Phe  Ile  Ala  Asp  Phe  Pro  Gly  Leu  His  Leu  Glu  Asn  Phe  Val
     530                     535                     540

Ser  Glu  Asp  Leu  Gly  Asn  Thr  Ser  Ile  Gln  Leu  Leu  Gln  Gly  Glu  Val
545                      550                     555                          560

Thr  Val  Glu  Leu  Val  Ala  Glu  Gln  Lys  Asn  Gln  Thr  Leu  Arg  Glu  Gly
                    565                     570                     575

Glu  Lys  Met  Gln  Leu  Pro  Ala  Gly  Glu  Tyr  His  Lys  Val  Tyr  Thr  Thr
               580                     585                     590

Ser  Pro  Ser  Pro  Ser  Cys  Tyr  Met  Tyr  Val  Tyr  Val  Asn  Thr  Thr  Glu
          595                     600                     605

Leu  Ala  Leu  Glu  Gln  Asp  Leu  Ala  Tyr  Leu  Gln  Glu  Leu  Lys  Glu  Lys
     610                     615                     620

Val  Glu  Asn  Gly  Ser  Glu  Thr  Gly  Pro  Leu  Pro  Pro  Glu  Leu  Gln  Pro
625                      630                     635                          640
```

-continued

| | | | | | | | | | | | | | | |
|---|---|---|---|---|---|---|---|---|---|---|---|---|---|---|
| Leu | Leu | Glu | Gly | Glu | Val | Lys | Gly | Gly | Pro | Glu | Pro | Thr | Pro | Leu | Val |
| | | | | 645 | | | | | 650 | | | | | 655 | |
| Gln | Thr | Phe | Leu | Arg | Arg | Gln | Gln | Arg | Leu | Gln | Glu | Ile | Glu | Arg | Arg |
| | | | 660 | | | | | 665 | | | | | 670 | | |
| Arg | Asn | Thr | Pro | Phe | His | Glu | Arg | Phe | Phe | Arg | Phe | Leu | Leu | Arg | Lys |
| | | 675 | | | | | 680 | | | | | 685 | | | |
| Leu | Tyr | Val | Phe | Arg | Arg | Ser | Phe | Leu | Met | Thr | Cys | Ile | Ser | Leu | Arg |
| | 690 | | | | | 695 | | | | | 700 | | | | |
| Asn | Leu | Ile | Leu | Gly | Arg | Pro | Ser | Leu | Glu | Gln | Leu | Ala | Gln | Glu | Val |
| 705 | | | | | 710 | | | | | 715 | | | | | 720 |
| Thr | Tyr | Ala | Asn | Leu | Arg | Pro | Phe | Glu | Ala | Val | Gly | Glu | Leu | Asn | Pro |
| | | | | 725 | | | | | 730 | | | | | 735 | |
| Ser | Asn | Thr | Asp | Ser | Ser | His | Ser | Asn | Pro | Pro | Glu | Ser | Asn | Pro | Asp |
| | | | 740 | | | | | 745 | | | | | 750 | | |
| Pro | Val | His | Ser | Glu | Phe | | | | | | | | | | |
| | | 755 | | | | | | | | | | | | | |

VITAMIN K-DEPENDENT CARBOXYLASE

This work was supported by grant HL06350-29 from the National Institutes of Health. The government has certain rights to this invention.

RELATED APPLICATIONS

This application is a continuation-in-part of copending application Ser. No. 07/697,427, filed May 8, 1991, now abandoned.

FIELD OF THE INVENTION

This invention relates to DNA sequences encoding enzymes, known as the vitamin K dependent carboxylases, which carry out the γ-carboxylation of glutamic acid residues in vitamin K dependent proteins such as Factor VII, Factor IX, Factor X, Protein C, Protein S, and Prothrombin.

BACKGROUND OF THE INVENTION

A number of blood coagulation proteins require a post-translational, vitamin K-dependent modification for biological activity. In 1974, Stenflo et al., Nelsestuen et al. and Magnusson et al. reported that the prototype of these vitamin K-dependent proteins, prothrombin, contained the modified amino acid, γ-carboxyglutamic acid (Gla). See J. Stenflo et al., *Proc. Natl. Acad. Sci. USA* 71:2730-2733 (1974); G. Nelsestuen et al., *J. Biol. Chem.* 249:6347-6350 (1974); S. Magnusson et al.. *FEBS Lett.* 44:189-193. (1974). Prothrombin from animals treated with the vitamin K antagonist warfarin lacked this Gla modification. It was inferred from these observations that the blood-clotting activity of the vitamin K-dependent proteins required γ-carboxylation of specific glutamic acid residues. Shortly thereafter, Esmon et al. demonstrated an enzyme activity, vitamin K-dependent carboxylase (hereafter called carboxylase), capable of making this Gla modification. See C. Esmon et al., *J. Biol. Chem.* 250:4744-4748 (1975).

After cDNA sequences were obtained for several of the vitamin K-dependent proteins, Pan and Price compared the deduced amino-acid sequences and suggested that the propeptide consensus sequence preceding the amino terminus of the vitamin K-dependent protein was a recognition site for the carboxylase See L. Pan and P. Price, *Proc. Natl. Acad. Sci. USA* 82:6109-6113 (1985). This suggestion was confirmed by Knobloch and Suttie, who demonstrated the importance of the propeptide in carboxylation by showing that the synthetic propeptide sequence of human factor X stimulated the activity of the carboxylase for a small substrate (Boc-Glu-Glu-Leu-OMe) in vitro. J. Knobloch and J. Suttie, *J. Biol. Chem.* 262:16157-16163 (1987). Jorgensen extended this observation by showing that factor IX with its propeptide deleted was not carboxylated. M. Jorgensen et al., *Cell* 48:185-191 (1987).

In spite of its importance, the carboxylase has not been previously purified. Purification of 400-fold has been reported. See J.-M. Girardot, *J. Biol. Chem.* 257:15008-15011 (1982). Comparison of Girardot's results to later purifications is complicated because, in our hands, ammonium sulfate and the propeptide stimulate the incorporation of $CO_2$ into the synthetic peptide substrate FLEEL by 13-fold. If one corrects for the lack of ammonium sulfate and propeptide in Girardot's assay mix, then he achieved a specific activity of $1.1 \times 10^7$ cpm/mg/hr. Soute et al. demonstrated that an immobilized factor X antibody would bind the carboxylase, presumably through a factor X precursor-carboxylase complex, and that the bound carboxylase retained its activity for the synthetic peptide substrate FLEEL. See B. Soute et al., *Biochem, Biophys. Acta.* 676:101-107 (1981). Harbeck et al. extended this method by eluting the carboxylase from a prothrombin antibody column with a synthetic propeptide achieving a 500-fold purification and a final specific activity of $6.6 \times 10^6$ cpm/mg/hr. See M. Harbeck et al., *Thromb. Res.* 56:317-323 (1989). Hubbard et al. reported the purification of the carboxylase to homogeneity using a synthetic propeptide sequence as an affinity ligand. See B. Hubbard et al., *Proc. Natl. Acad. Sci. USA* 86:6893-6897 (1989). However, the reported final specific activity, $1.3 \times 10^7$ cpm/mg/hr, was still not significantly different than that reported by Girardot. Numerous studies with the crude carboxylase have yielded important information about its properties and mode of action. See J. Suttie, *Ann. Rev. Biochem.* 54:459-77 (1985). It is clear, however, that for detailed mechanistic studies and physical characterization of the enzyme, purification is necessary.

We recently reported the production in *E. coli* of four different 59-residue peptides containing the propeptide and Gla domain of human factor IX. See S.-M. Wu et al., *J. Biol. Chem.* 265:13124-13129 (1990). We report here that one of these peptides, FIXQ/S (SEQ ID NO:1), is an excellent affinity ligand for purification of the carboxylase. A 7,000-fold purification of the carboxylase to approximately 80%-90% apparent purity and final specific activity of about $2.4 \times 10^9$ cpm/mg/hr was obtained. The apparent molecular weight was 94,000 by reducing SDS-PAGE analysis.

SUMMARY OF THE INVENTION

A first aspect of the present invention is isolated DNA encoding a vitamin K dependent carboxylase selected from the group consisting of: a) isolated DNA selected from the group consisting of DNA which encodes bovine vitamin K dependent carboxylase and DNA which encodes human vitamin K dependent carboxylase; (b) isolated DNA which hybridizes to isolated DNA of (a) above and which encodes a vitamin K dependent carboxylase; and (c) isolated DNA differing from the isolated DNAs of (a) and (b) above in nucleotide sequence due to the degeneracy of the genetic code, and which encodes a vitamin K dependent carboxylase.

A second aspect of the present invention is a recombinant DNA sequence comprising vector DNA and a DNA according encoding vitamin K dependent carboxylase as given above.

A third aspect of the present invention is a host cell containing a recombinant DNA sequence as given above and capable of expressing the encoded vitamin K dependent carboxylase.

A fourth aspect of the present invention is an improved method of making a vitamin K dependent protein. The method comprises culturing a host cell which expresses a vitamin K dependent protein in the presence of vitamin K; and then harvesting said vitamin K dependent protein from the culture. The improvement comprises employing as the host cell a host cell which contains a recombinant DNA sequence comprising vector DNA operable in the host cell and a DNA encoding a vitamin K dependent carboxylase selected from the group consisting of: (a) isolated DNA selected from the group consisting of DNA which encodes bovine vitamin K dependent carboxylase and DNA which encodes human vitamin K dependent carboxylase; (b) isolated DNA which hybridizes to isolated DNA of (a) above and which encodes a vitamin K dependent carboxylase; and (c) isolated DNA differing from the isolated DNAs of (a) and (b) above in nucleotide sequence due to the degeneracy of the genetic code, and which encodes a vitamin K dependent carboxylase.

The foregoing and other aspects of the present invention are explained in detail in the drawings, Examples, and Detailed Description set forth below.

DETAILED DESCRIPTION OF THE INVENTION

Figure 1:
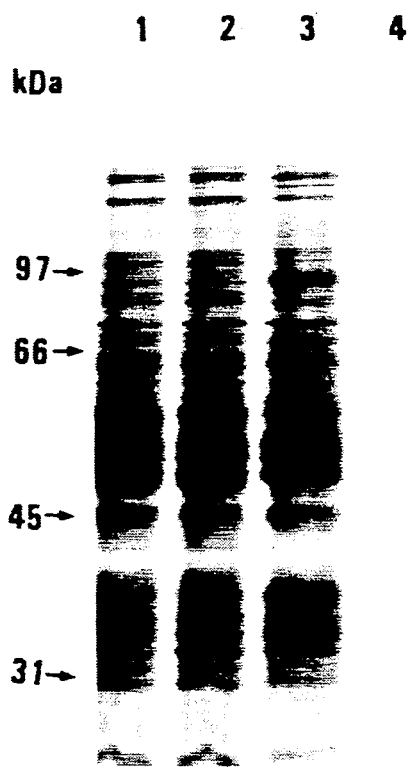
FIG. 1. Silver-stained, 10% reducing SDS-PAGE analysis of Affi-FIXQ/S purified carboxylase preparations to demonstrate the effect of sonication. The counts reflect the carboxylase activity in each lane. Lane 1 is the sonicated loading material (380 cpm/30 min); lane 2 is the sonicated flow-through (265 cpm/30 min); lane 3 is unsonicated elution I carboxylase preparation (23,500 cpm/30 min); lane 4 is sonicated elution I carboxylase preparation (5000 cpm/30 min).

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., PatentIn User Manual, 99-102 (Nov. 1990)(U.S. Patent and Trademark Office, Office of the Assistant Commissioner for Patents, Washington, D.C. 20231); U.S. Pat. No. 4,871,670 to Hudson et al. at Col. 3 lines 20-43 (applicants specifically intend that the disclosure of this and all other patent references cited herein be incorporated herein by reference).

A. Genetic Engineering Techniques

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

A vector is a replicable DNA construct. Vectors are used herein either to amplify DNA encoding Vitamin K Dependent Carboxylase and/or to express DNA which encodes Vitamin K Dependent Carboxylase. An expression vector is a replicable DNA construct in which a DNA sequence encoding Vitamin K Dependent Carboxylase is operably linked to suitable control sequences capable of effecting the expression of Vitamin K Dependent Carboxylase in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence;

or a ribosome binding site is operably linked to a coding sequence if it is positioned so as to permit translation.

Transformed host cells are cells which have been transformed or transfected with Vitamin K Dependent Carboxylase vectors constructed using recombinant DNA techniques. Transformed host cells ordinarily express Vitamin K Dependent Carboxylase, but host cells transformed for purposes of cloning or amplifying Vitamin K Dependent Carboxylase DNA do not need to express Vitamin K Dependent Carboxylase.

Suitable host cells include prokaryote, yeast or higher eukaryotic cells such as mammalian cells and insect cells. Cells derived from multicellular organisms are a particularly suitable host for recombinant Vitamin K Dependent Carboxylase synthesis, and mammalian cells are particularly preferred. Propagation of such cells in cell culture has become a routine procedure (Tissue Culture, Academic Press, Kruse and Patterson, editors (1973)). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the DNA encoding vitamin K dependent Carboxylase to be expressed and operatively associated therewith, along with a ribosome binding site, an RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See. e.g.. U.S. Pat. No. 4,599,308.

An origin of replication may be provided either by construction of the vector to include an exogenous origin, such as may be derived from SV 40 or other viral (e.g. Polyoma, Adenovirus, VSV, or BPV) source, or may be provided by the host cell chromosomal replication mechanism. If the vector is integrated into the host cell chromosome, the latter is often sufficient.

Rather than using vectors which contain viral origins of replication, one can transform mammalian cells by the method of cotransformation with a selectable marker and the Vitamin K Dependent Carboxylase DNA. Examples of suitable selectable markers are dihydrofolate reductase (DHFR) or thymidine kinase. This method is further described in U.S. Pat. No. 4,399,216.

Other methods suitable for adaptation to the synthesis of Vitamin K Dependent Carboxylase in recombinant vertebrate cell culture include those described in M-J. Gething et al., Nature 293, 620 (1981); N. Mantei et al., Nature 281, 40; A. Levinson et al., EPO Application Nos. 117,060A and 117,058A.

Host cells such as insect cells (e.g., cultured Spodoptera frugiperda cells) and expression vectors such as the baculovirus expression vector (e.g., vectors derived from Autographa californica MNPV, Trichoplusia ni MNPV, Rachiplusia ou MNPV, or Galleria ou MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Prokaryote host cells include gram negative or gram positive organisms, for example Escherichia coli (E. coli) or Bacilli. Higher eukaryotic cells include established cell lines of mammalian origin as described below. Exemplary host cells are E. coli W3110 (ATCC 27,325), E. coli B, E. coli X1776 (ATCC 31,537), E. coli 294 (ATCC 31,446). A broad variety of suitable prokaryotic and microbial vectors are available. E. coli is typically transformed using pBR322. Promoters most commonly used in recombinant microbial expression vectors include the betalactamase (penicillinase) and lactose promoter systems (Chang et al., Nature 275, 615 (1978); and Goeddel et al., Nature 281, 544 (1979)), a tryptophan (trp) promoter system (Goeddel et al., Nucleic Acids Res. 8, 4057 (1980) and EPO App. Publ. No. 36,776) and the tac promoter (H. De Boer et al., Proc. Natl. Acad. Sci. USA 80, 21 (1983)). The promoter and Shine-Dalgarno sequence (for prokaryotic host expression) are operably linked to the DNA encoding the Vitamin K Dependent Carboxylase, i.e., they are positioned so as to promote transcription of Vitamin K Dependent Carboxylase messenger RNA from the DNA.

Eukaryotic microbes such as yeast cultures may also be transformed with Vitamin K Dependent Carboxylase-encoding vectors. see, e.g., U.S. Pat. No. 4,745,057. Saccharomyces cerevisiae is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding Vitamin K Dependent Carboxylase, sequences for polyadenylation and transcription termination, and a selection gene. An exemplary plasmid is YRp7, (Stinchcomb et al., Nature 282, 39 (1979); Kingsman et al., Gene 7, 141 (1979); Tschemper et al., Gene 10, 157 (1980)). Suitable promoting sequences in yeast vectors include the promoters for metallothionein, 3-phosphoglycerate kinase (Hitzeman et al., J. Biol. Chem. 255, 2073 (1980) or other glycolytic enzymes (Hess et al., J. Adv. Enzyme Reg. 7, 149 (1968); and Holland et al., Biochemistry 17, 4900 (1978)). Suitable vectors and promoters for use in yeast expression are further described in R. Hitzeman et al., EPO Publn. No. 73,657.

B. Vitamin K-Dependent Carboxylase

Carboxylase enzymes of the present invention include proteins homologous to, and having essentially the same biological properties as, the bovine vitamin K dependent carboxylase and the human vitamin K dependent carboxylase disclosed herein. This definition is intended to encompass natural allelic variations in the carboxylase enzymes. Cloned genes of the present invention may code for carboxylase enzyme of any species of origin, including mouse, rat, rabbit, cat, porcine, and human, but preferably code for carboxylase enzyme of mammalian origin. Thus, DNA sequences which hybridize to DNA which encodes bovine or human vitamin K dependent carboxylase and which code on expression for a vitamin K dependent carboxylase are also an aspect of this invention. Conditions which will permit other DNA sequences which code on expression for a vitamin K dependent carboxylase to hybridize to the DNA sequence of bovine or human vitamin K dependent carboxylase can be determined in a routine manner. For example, hybridization of such sequences may be carried out under conditions of reduced stringency or even stringent conditions (e.g., conditions represented by a wash stringency of 0.3M NaCl, 0.03M sodium citrate, 0.1% SDS at 60° C. or even 70° C. to DNA encoding the bovine or human vitamin K dependent carboxylase disclosed herein in a standard in situ hybridization assay. See J. Sambrook et al., Molecular Cloning, A Laboratory Manual (2d Ed. 1989)(Cold Spring Harbor Laboratory)). In general, sequences which code for vitamin K dependent carboxylase and hybridize to the DNA encoding bovine or human vitamin K dependent carboxylase disclosed herein will be at least 75% homologous, 85% homologous, or even 95% homologous or more with the sequence of the bovine or huaman vitamin K dependent carboxylase disclosed herein. Further, DNA sequences which code for bovine or human vitamin K dependent carboxylase, or sequences which code for a carboxylase coded for by a sequence which hybridizes to the DNA sequence which codes for bovine or human vitamin K dependent carboxylase, but which differ in codon sequence from these due to the degeneracy of the genetic code, are also an aspect of this invention. The degeneracy of the genetic code, which allows different nucleic acid sequences to code for the same protein or peptide, is well known in the literature. See e.g., U.S. Pat. No. 4,757,006 to Toole et al. at Col. 2, Table 1.

By providing the purification procedure set forth below, and making available cloned genes which encode vitamin K dependent carboxylase, the present invention makes available vitamin K dependent carboxylase with purities of at least 80% (percent by weight of total protein), at least 90%, and more. Purified carboxylase of the present invention is useful for carboxylating vitamin K dependent enzymes to increase the activity thereof. The carboxylase enzyme may be purified from lysed cell fractions or microsomes containing the enzyme in accordance with the procedures described herein, optionally followed by other techniques such as ion exchange chromatography. See generally Enzyme Purification and Related Techniques, *Methods in Enzymology* 22, 233–577 (1977).

C. Vitamin K-Dependent Proteins

Numerous vitamin K-dependent proteins can be carboxylated with the carboxylase disclosed herein. A preferred group of vitamin K-dependent proteins for practicing the present invention is the blood coagulation proteins, including, but not limited to, Factor VII, Factor IX, Factor X, Protein C, Protein S, and Prothrombin.

As noted above, the present invention provides a method of carboxylating vitamin K dependent proteins by coexpressing the vitamin K dependent protein and the vitamin K dependent carboxylase disclosed herein in a single host cell. In general, the method comprises culturing a host cell which expresses a vitamin K dependent protein in the presence of vitamin K; and then harvesting the vitamin K dependent protein from the culture. The host cell further contains a recombinant DNA sequence comprising vector DNA operable in the host cell and a DNA encoding a vitamin K dependent carboxylase as described herein. While some host cells may carboxylate the vitamin K dependent protein at basal levels, the vector DNA encoding vitamin K dependent carboxylase is included to enhance carboxylation. The culture can be carried out in any suitable fermentation vessel, with a growth media and under conditions appropriate for the expression of the vitamin K dependent carboxylase and vitamin K dependent protein by the particular host cell chosen. The vitamin K dependent protein harvested from the culture is found to be carboxylated due to the expression of the vitamin k dependent carboxylase in the host cell. The vitamin K dependent protein can be expressed in the host cell by any of the means described above for expressing the vitamin K dependent carboxylase in the host cell (e.g., by transforming the host cell with an expression vector such as a plasmid comprising DNA which encodes the vitamin K dependent protein). The vitamin K dependent protein can be collected directly from the culture media, or the host cells lysed and the vitamin K dependent protein collected therefrom. The vitamin K dependent protein can then be further purified in accordance with known techniques.

Factor VII DNA sequences, along with vectors and host cells for expression thereof, are disclosed in U.S. Pat. No. 4,784,950 to F. Hagen et al.

Factor IX DNA coding sequences, along with vectors and host cells for the expression thereof, are disclosed in European Patent App. 373012, European Patent App. 251874, PCT Patent Appl. 8505376, PCT Patent Appln. 8505125, European Patent Appln. 162782, and PCT Patent Appln. 8400560.

Factor X purification is disclosed in U.S. Pat. No. 4,411,794 to H. Schwinn et al.

Protein C DNA coding sequences, along with vectors and host cells for the expression thereof, are disclosed in U.S. Pat. No. 4,992,373 to N. Bang et al., U.S. Pat. No. 4,968,626 to D. Foster and E. Davie, and U.S. Pat. No. 4,959,318 to D. Foster et al.

Protein S DNA coding sequences, along with vectors and host cells for the expression thereof, are disclosed in European Patent Appln. 255771 and European Patent Appln. 247843.

Prothrombin purification is disclosed in Japanese Kokai 2019400.

D. Expression of Vitamin-K Dependent Carboxylase in Mammalian Milk

Another aspect of the present invention is transgenic mammals (e.g., cows, goats, pigs) containing an expression system comprising a suitable promoter, such as a casein promoter, operatively linked to a DNA sequence coding for vitamin K dependent carboxylase as disclosed herein through a DNA sequence coding for a signal peptide effective in secreting the carboxylase in mammary tissue. Such animals provide for a process of producing the carboxylase enzyme in which milk can be collected from the animals and the carboxylase enzyme isolated from the milk. The carboxylase coding sequence may be modified to render it soluble, as discussed below. The carboxylase isolated from the milk can then be used, among other things, to carboxylase vitamin K dependent proteins in vitro. In the alternative, vitamin K-dependent proteins can be co-expressed with the vitamin K dependent carboxylase in such transgenic animals in like manner, through a like expression system, and the carboxylated proteins collected from the milk. Such animals can be produced and such processes can be carried out in accordance with known procedures. See, e.g., U.S. Pat. No. 4,873,316 to H. Meade and N. Lonberg, titled "Isolation of Exogenous Recombinant Proteins from the Milk of Transgenic Mammals"; U.S. Pat. No. 4,873,191 to T. Wagner and P. Hoppe, titled "Genetic Transformation of Zygotes."

E. Additional Applications of the Invention

Because the best marker for human liver carcinoma is increased levels of undercarboxylated prothrombin, hybridization probes for mRNA levels of carboxylase are useful for diagnosis of liver cancer, as discussed in detail below. As also discussed below, antibodies to the carboxylase may be prepared, labelled with a suitable detectable group, and used to diagnose altered patterns of expression of the carboxylase enzyme in a subject (e.g., a patient potentially afflicted with liver carcinoma). Antibodies can also be used to immobilize the carboxylase for in-vitro carboxylation of undercarboxylated proteins. Furthermore, one can express a soluble form of the carboxylase to enable the in vitro modification of undercarboxylated proteins.

Hybridization probes of the present invention may be cDNA fragments or oligonucleotides, and may be labelled with a detectable group as discussed hereinbelow. The probes selectively bind to mRNA encoding vitamin K-dependent carboxylase. Pairs of probes which will serve as PCR primers for carboxylase mRNA or a portion thereof may be used in accordance with the process described in U.S. Pat. Nos. 4,683,202 and 4,683,195, or modifications thereof which will be apparent to those skilled in the art.

As noted above, the present invention provides for an aqueous solution having the carboxylase enzyme solubilized therein. Soluble carboxylase enzyme may be made by deleting the transmembrane region of the carboxylase cDNA, then expressing the altered enzyme, and then collecting the altered enzyme for solubilization in an aqueous solution. The choice of aqueous solution is not critical, with the solution chosen simply being one appropriate for carrying out the carboxylation of vitamin K dependent proteins in vitro. By "deletion" of the transmembrane region of the cDNA, we mean removal or alteration of a sufficient portion of the hydrophobic transmembrane domain to render the coded-for enzyme soluble in an aqueous solution.

A variety of detectable groups can be employed to label antibodies and probes as disclosed herein, and the term "labelled" is used herein to refer to the conjugating or covalent bonding of any suitable detectable group, including enzymes (e.g., horseradish peroxidase, $\beta$-glucuronidase, alkaline phosphatase, and $\beta$-D-galactosidase), fluorescent labels (e.g., fluorescein, luciferase), and radiolabels (e.g., $^{14}C$, $^{131}I$, $^{3}H$, $^{32}P$, and $^{35}S$) to the compound being labelled. Techniques for labelling various compounds, including proteins, peptides, and antibodies, are well known. See, e.g., Morrison, *Methods in Enzymology* 32b, 103 (1974); Syvanen et al., *J. Biol. Chem.* 284, 3762 (1973); Bolton and Hunter, *Biochem. J.* 133, 529 (1973).

Antibodies which specifically bind to the carboxylase enzyme (i.e., antibodies which bind to a single antigenic site or epitope on the carboxylase enzyme) may be polyclonal or monoclonal in origin, but are preferably of monoclonal origin. The antibodies are preferably IgG antibodies of any suitable species, such as rat, rabbit, or horse, but are generally of mammalian origin. Fragments of IgG antibodies which retain the ability to specifically bind the carboxylase enzyme, such as $F(ab')_2$, $F(ab')$, and Fab fragments, are intended to be encompassed by the term "antibody" herein. The antibodies may be chimeric, as described by M. Walker et al., *Molecular Immunol.* 26, 403 (1989). Antibodies may be immobilized on a solid support of the type used as a packing in an affinity chromatography column, such as sepharose, silica, or glass beads, in accordance with known techniques.

Monoclonal antibodies which bind to carboxylase enzyme are made by culturing a cell or cell line capable of producing the antibody under conditions suitable for the production of the antibody (e.g., by maintaining the cell line in HAT media), and then collecting the antibody from the culture (e.g., by precipitation, ion exchange chromatography, affinity chromatography, or the like). The antibodies may be generated in a hybridoma cell line in the widely used procedure described by G. Kohler and C. Milstein, *Nature* 256, 495 (1975), or may be generated with a recombinant vector in a suitable host cell such as *Escherichia coli* in the manner described by W. Huse et al., Generation of a Large Combinatorial Library of the Immunoglobulin Repertoire in Phage Lambda, *Science* 246, 1275 (1989).

The present invention is explained in greater detail in the following non-limiting examples. In the examples, mmol means millimoles; ml means milliliters; mCi means milliCuries; $\mu g$ means micrograms; $\mu M$ means microMolar; gm means grams; hr means hours; cpm means counts per minute; MOPS means 4-Morpholinepropanesulfonic acid; and CHAPS means 3-[(3-cholamidopropyl)dimethylammonio]-1-propanesulfonate. Temperatures are given in degrees Centigrade.

EXAMPLE 1

Purification to Near Homogeneity of the Vitamin K-dependent Carboxylase

All chemicals used herein are reagent grade. 3,3'-Dithiobis(sulfosuccinimidylpropionate) (DTSSP) was purchased from Pierce Chemical Co. Aprotinin and Pepstatin A were purchased from Boehringer Mannheim Biochemicals. Leupeptin, phenylmethylsulfonyl fluoride (PMSF), and (3-((3-Cholamidopropyl)-dimethylammonio)-1-propanesulfonate (CHAPS) were obtained from Sigma. The peptide FLEEL and the protease inhibitors FFRCK and FPRCK were from Bachem. Peptide proFIX19, AVFLDHENANKILNRPKRY, was synthesized by Frank Church of UNC-CH. $NaH^{14}CO_3$, specific activity 50.0 mCi/mmol, was from NEN and Aqua Mephyton from Merck Sharp and Dohme. Protease inhibitor cocktail (PIC) was freshly prepared as a $10 \times$ PIC shock with 20 mM dithiothreiotol, 20 mM EDTA, 1.25 $\mu g$/ml FFRCK, 1.25 $\mu g$/ml FPRCK, 5 $\mu g$/ml Leupeptin, 7 $\mu g$/ml Pepstatin A, 340 $\mu g$/ml PMSF, and 20 $\mu g$/ml Aprotinin.

Preparation of Affinity Column. Peptide FIXQ/S SEQ ID NO:1)(residues $-18$ to 41 of factor IX with mutations Arg to Glu at residue $-4$ and Arg to Ser at residue $-1$) was chosen for the affinity ligand because its affinity for the carboxylase is not changed and because it has fewer trypsin cleavage sites than our other peptides and is therefore less likely to be degraded by proteases in the crude extracts used for purification. Peptide FIXQ/S was prepared according to S.-M. Wu et al. supra. One hundred mg of FIXQ/S was coupled to 25 ml of Affi-Gel 10 (Bio-Rad Inc.) according to the manufacturer. The reaction was done at pH 4.8, which is one unit below the theoretical pI of FIXQ/S. The final concentration of the covalently bound FIXQ/S on Affi-Gel 10 was measured as 442 μM and the coupled ligand is referred to as Affi-FIXQ/S.

Affinity Purification of Carboxylase. Preparation of microsomes from bovine liver, solubilization of microsomes, and ammonium-sulfate fractionation were as described by Girardot (supra). Protein concentration was measured with the Bio-Rad protein assay kit. See M. Bradford, *Anal. Biochem.* 72:248-254 (1976). Alternatively, protein concentration and relative purity were determined by scanning of SDS-PAGE gels stained with silver or Coomassie blue. See U. Laemmli, *Nature* 227:680-685 (1970); H. Blum, et al., *Electrophoresis* 8:93-99 (1987). In all cases, reference curves were prepared with IgG as a standard. Ammonium-sulfate fractionated microsomal protein (7-8 gm) was resuspended in buffer A (25 Mm MOPS, pH 7.0, 500 mM NaCl, 20% glycerol, 0.1% phosphatidylcholine, and 1×PIC) with 0.1% CHAPS to a total volume of 150 ml. In all purification experiments, except that depicted in lane 3 of FIG. 1, the suspension was sonicated with a standard ultrasonic probe (Sonicator Model W-220F, Heat Systems Inc.) at scale 9 for 100 2-second pulses in an ice bath. The sonicated material was loaded on a 25-ml Affi-FIXQ/S column equilibrated with 150 ml of 0.1% CHAPS in buffer A at 4° C. at a flow rate of 10 ml/hr. The loaded column was washed with 100-200 ml of 0.1% CHAPS in buffer A. The carboxylase was eluted from the Affi-FIXQ/S column by one of the following methods.

Elution I. 150 μM propeptide in buffer A with 0.1% CHAPS was used to elute the carboxylase. The column was filled with eluant and incubated overnight before collecting the eluate. The propeptide eluate was concentrated with Centricon-30 (Amicon Inc.); the filtrate could be reused for elution. Significant amounts of carboxylase activity were continuously eluted for a week.

Elution II. A flow rate of 10 ml/hr was used for all chromatography steps. An extensive wash was carried out by two sequential steps: 100 ml of 0.05% to 0.85% Triton X-100 gradient in buffer B (25 mM MOPS, pH 7.0, 50 mM NaCl, 20% glycerol, 0.1%, and 1×PIC) containing 0.2% phosphatidylcholine followed by 100 ml of 0.1% to 1% CHAPS gradient in buffer B containing 0.1% phosphatidylcholine. Elution was accomplished by using 100 ml of a double gradient of 0.1% to 1% CHAPS and 0 to 2 μM proFIX19 in buffer A and continued with another 100 ml of 1% CHAPS and 2 μM proFIX19 in buffer A.

CM-Sepharose Chromatography, Desalted, concentrated carboxylase (total activity of $2.2 \times 10^7$ cpm/30 min) eluted by method I was prepared in buffer C (25 mM MOPS, ph 7.0, 100 mM NaCl, 20% glycerol, 1×PIC), with 1% Triton X-100, 0.7% phosphatidylcholine, and to a total volume of 3.85 ml. This carboxylase preparation was then sonicated in a bath sonicator for 24 5-second pulses and batch adsorbed to 5.8 ml of CM Sepharose. The CM Sepharose was packed into a column, washed, and eluted with a 10 ml of NaCl gradient from 100 mM to 450 mM in buffer C with 0.05% Triton X-100, 0.2% phosphatidylcholine.

Cross-Linking Reaction. The cross-linking was accomplished with (DTSSP) as described by S. Jung and M. Moroi, *Biochem. Biophys. Acta* 761:152-162 (1983). For competition experiments, 100-fold excess of proFIX19 was included.

Carboxylase assay. The assay was done for 30 min as described in S.-M. Wu et al., supra, in 25 mM MOPS, pH 7.0, 500 mM NaCl, with 0.16% CHAPS/phosphatidylcholine. FLEEL at 3.6 mM and 5 μCi NaH$^{14}$CO$_3$ were the substrates; 0.8M ammonium sulfate and 16 μM proFIX19 were included as activators.

Identification of the Carboxylase. FIG. 1 displays a reducing SDS-PAGE analysis of our initial Affi-FIXQ/S purification of carboxylase. There is little difference between the protein pattern of the starting material and the flow-through (lane 1 and lane 2). The sample in lane 3 represents protein eluted with 150 μM proFIX19. There is some enhancement of a protein band at 94,000 M$_r$ but the purification achieved is only 60-fold. We reasoned that the poor purification might be the result of large micelles which contained at least one carboxylase molecule as well as other integral membrane proteins. The carboxylase molecule would allow binding to the affinity matrix but the other proteins would be co-eluted with the carboxylase. We tried to apply the standard solution to this problem, which is to increase the detergent concentration until one protein per micelle is achieved. However, the carboxylase would not bind to Affi-FIXQ/S in the presence of a high concentration of a number of detergents. Therefore, we sought to reduce the micelle size by sonicating the starting material. As shown in FIG. 1, lane 4, the relative intensity of the 94,000-M$_r$ band in the proFIX19 eluate is much more prominent after sonication. Furthermore, the amount of carboxylase bound to Affi-FIXQ/S increased from 15% to 30% and the purification increased to 500-fold.

Figure 2:
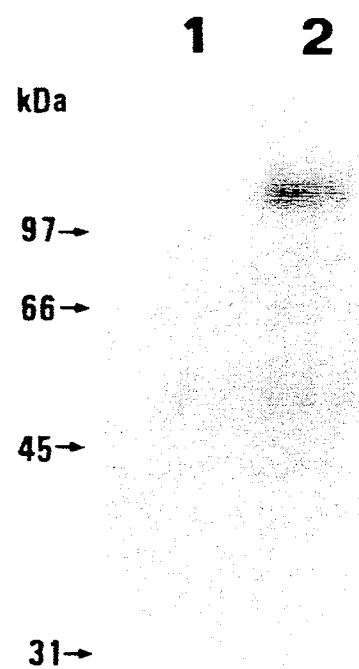
FIG. 2. Autoradiogram of cross-linking between $^{125}$I-FIXQ/S and protein from the partially-purified carboxylase preparation shown in FIG. 1, lane 3. Proteins were separated by 10% non-reducing SDS-PAGE. Lane 1 is proFIX19 competition of cross-linking; lane 2 is cross-linking in absence of proFIX19.

In order to evaluate the binding specificity of FIXQ/S and attain an independent estimate of the molecular weight of the carboxylase, we cross-linked $^{125}$I-FIXQ/S to 60-fold affinity-purified material (FIG. 1, lane 3). The autoradiogram in FIG. 2, lane 2 shows one major band, slightly larger than 97,000 M$_r$, which represents the complex of the cross-linked protein and the synthetic peptide $^{125}$I-FIXQ/S. This major band was eliminated when the same experiment was run in the presence of excess non-radioactive proFIX19 (FIG. 2, lane 1). The minor bands in lane 2 were unaffected by competition (lane 1). By subtracting the molecular weight of FIXQ/S (7,000 M$_r$) from the estimated size of the cross-linked complex we estimate that the size of the protein to which the FIXQ/S peptide binds is approximately 94,000 M$_r$. This agrees with the size of the band enriched in each of the early purifications (FIG. 1), indicating that the 94,000-M$_r$ protein (lanes 3 and 4) is the enzyme carboxylase and that the interaction between the peptide FIXQ/S and carboxylase is very specific.

Figure 3:
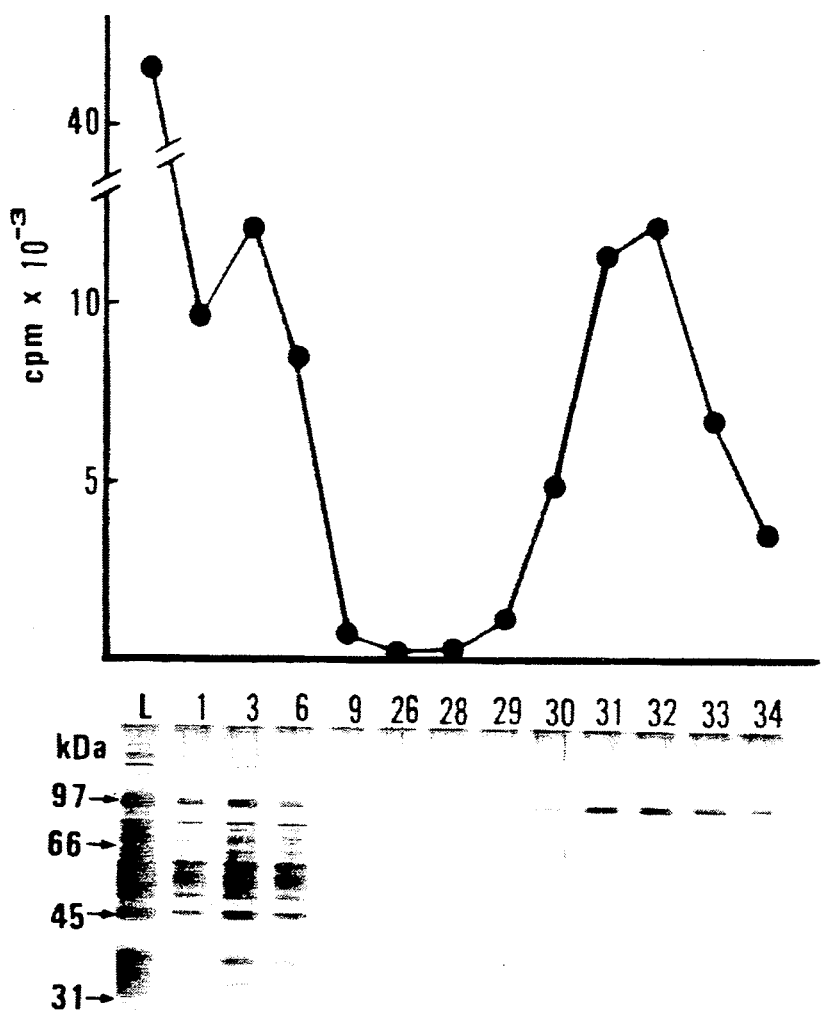
FIG. 3. Activity profile and reducing SDS-PAGE analysis (10%, silver-stained) of fractions from CM-Sepharose chromatography. The fraction numbers are on the X-axis. 7.5 μl from each fraction was analyzed by SDS-PAGE. The counts, shown on the Y-axis, represent the carboxylase activity in each lane. The carboxylase activity was determined by the $^{14}CO_2$ incorporation into FLEEL in the standard assay. L is loading material; fractions 1-7 are flow-through; fractions 8-27 are wash; fractions 28-37 are elution.

Results shown in FIG. 3 indicate that further purification can be achieved by chromatography of the 500-fold affinity-purified material on CM Sepharose. Resolubilization, sonication, and batch adsorption on CM sepharose followed by elution with a salt gradient produced a dramatic improvement in purification. The batch adsorption step is very important as enzymatic activity is lost and significantly less purification is achieved when the material is adsorbed to the top of the column. However, the most important information in this figure is that the carboxylase activity in each fraction is proportional to the amount of 94,000-M$_r$ protein in the corresponding SDS-PAGE analysis. Quantitation of the silver-stained gel by scanning reveals that the protein is 80-90% pure. The specific activity is $2 \times 10^9$ cpm/mg/hr.

Figure 4:
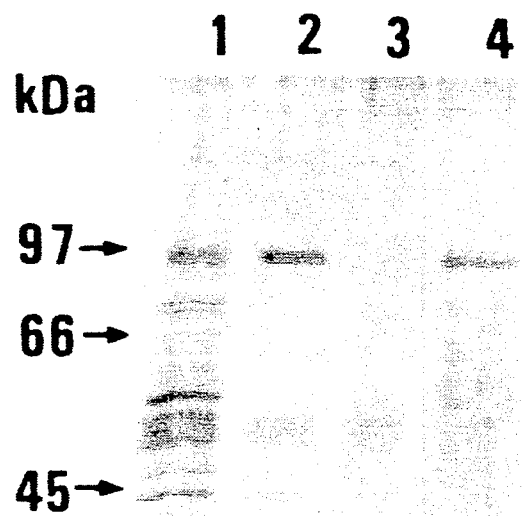
FIG. 4. Silver-stained, 10% reducing SDS-PAGE analysis of a CM-purified carboxylase re-chromatographed on Affi-FIXQ/S to show the correlation between the 94,000 $M_r$ protein and activity. Lane 1 is the first Affi-FIXQ/S carboxylase preparation (9750 cpm/30 min); lane 2 is purified CM eluate (6729 cpm/30 min, used for the second Affi-FIXQ/S); lane 3 is flow-through of the second Affi-FIXQ/S (394 cpm/30 min); lane 4 is sample of second Affi-FIXQ/S elute (18853 cpm/30 min, eluate I method). The difference in activity between the carboxylase shown in lanes 2 and 4 is the result of some inactivation of the carboxylase of lane 2.

Further evidence that the 94,000-M$_r$ band represents the carboxylase is presented in FIG. 4. A carboxylase preparation purified by Affi-FIXQ/S and carboxymethyl sepharose (lane 2) was re-applied to the Affi-FIXQ/S column. Lane 3 shows that the activity of carboxylase was removed when the 94,000-$M_r$ protein bound to Affi-FIXQ/S. Lane 4 shows that the activity again co-eluted with the 94,000-$M_r$ protein. This carboxylase is from one of our earlier preparations and contained a significant amount of inactive carboxylase. This explains the observation that the amounts of protein in the 94,000 $M^r$ bands in lanes 2 and 4 are approximately equal while the activity is greater in the sample repurified by Affi-FIXQ/S; only active carboxylase binds to the affinity column.

Figure 5:
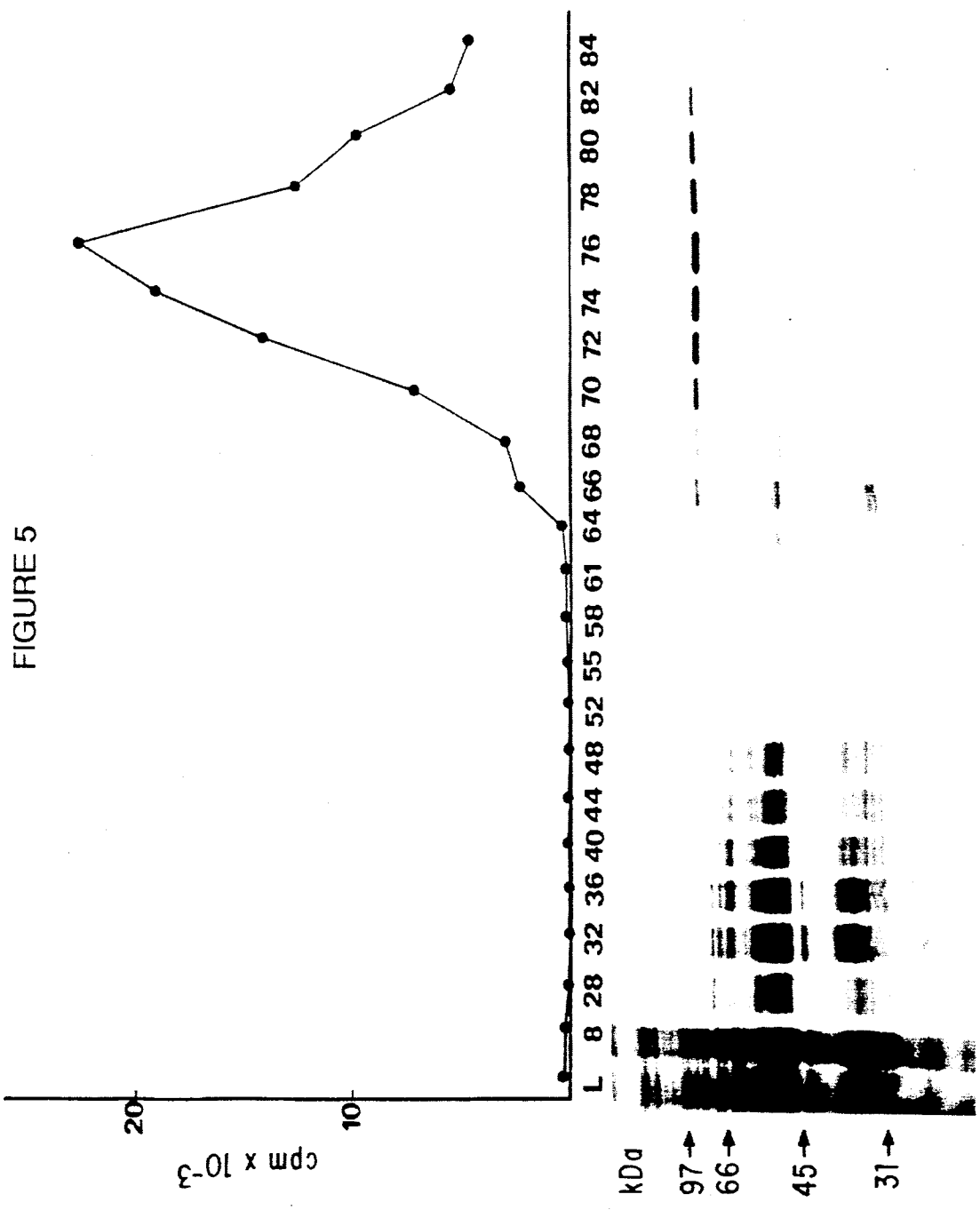
FIG. 5. Activity profile and reducing SDS-PAGE analysis (10%, silver-stained) of fractions from Affi-FIXQ/S chromatography elution II. 5.0 μl of each fraction was used for SDS-PAGE analysis except that the loading material and fraction 8 were diluted 100-fold before analysis. The fraction number is shown on the X-axis. The Y-axis represents the carboxylase activity in each lane. The carboxylase activity was determined by the $^{14}CO_2$ incorporation into FLEEL in the standard assay. L is loading material; fractions 1-20 are flow-through (because each fraction is equivalent, only one is shown); fractions 21-30 are wash; fractions 31-49 are Triton X-100 gradient; fractions 56-63 are CHAPS gradient; fractions 64-75 are CHAPS and proFIX19 double gradient; fractions 76-90 are 1% CHAPS/2 μM proFIX19 elution.

Purification of the Carboxylase. One of the problems with using the affinity column is that the elution using the propeptide is very slow and requires several days to achieve an adequate yield. We therefore explored alternative methods to elute the enzyme from the affinity column. As shown in FIG. 5, we were able to remove essentially all contaminating proteins without loss of carboxylase activity by washing the loaded affinity column extensively with Triton X-100 followed by a wash with CHAPS. The carboxylase could then be eluted with a gradient of CHAPS in a high concentration of NaCl (data not shown) or a gradient of CHAPS and propeptide containing a high concentration of NaCl (FIG. 5). The carboxylase activity coincides with the 94,000-$M_r$ protein profile. And, depending upon the fraction chosen, the carboxylase is 80 to 95% pure. If the propeptide is omitted from the elution gradient, the carboxylase in higher concentrations of CHAPS rapidly loses activity. Table 1 is the purification table for our final purification scheme. Note that 30% of the activity in the starting material is bound (obtained by subtracting the activity in the flow-through from the load) and that 34% of total activity is recovered by elution. Thus it appears that very little of the observed increase in specific activity is due to the removal of an inhibitor.

The major protein that coincides with the carboxylase activity in our preparation has a 94,000 $M_r$ in reducing SDS-PAGE analysis. This is very different from the 77,000 $M_r$ protein reported by Hubbard et al. (supra). Flynn et al. demonstrated that many different small peptides could be used for the single-step affinity purification of BiP (or glucose-regulated protein, or hsp 78) from solubilized microsomes. See G. Flynn, *Science* 245:385-390 (1989). Hubbard et al. (supra), using a similar starting material and a similar purification scheme, obtained a protein with the same molecular weight as BiP with a relatively low specific activity for carboxylase. We concluded that the 77,000-$M_r$ protein reported by Hubbard et al. was BiP, one of the most abundant proteins in the endoplasmic reticulum.

The method used in this Example for purification of the carboxylase may have general importance for the purification of membrane proteins. A basic strategy for purifying integral membrane proteins is to make micelles containing only one protein. However, high concentrations of detergent often result in the inactivation of the protein of interest. By appropriate sonication, one can create smaller mixed micelles without affecting the catalytic or binding ability of the protein. Because the immobilized protein is often more stable, the problems associated with mixed micelles can be solved by carefully choosing the conditions for washing the bound solid phase. This method of washing the bound protein with a high concentration of detergent should also be applicable to integral membrane proteins bound to standard ion exchange matrices.

Carboxylase is an integral membrane protein present in low concentrations that has previously resisted purification. To overcome the inherent difficulties, we chose affinity binding as the first purification step. By manipulating the biophysical properties of micelles we were able to achieve a single-step purification of carboxylase with 80-90% purity. Starting from 8 grams of microsomal protein, we can easily generate 300-400 μg of

TABLE 1

Purification of Carboxylase

| Sample | Total Protein | Total Carboxylase Acitivity (cpm/30 min) | Recovery of Activity | Specific Acitivity (cpm/mg/hr) | Purification-fold |
|---|---|---|---|---|---|
| Solubilized microsomes (load) | 8100 mg | $1.14 \times 10^9$ | 100% | $2.81 \times 10^5$ | 1 |
| Flow-through of Affi-FIXQ/S | 8090 mg | $8.08 \times 10^8$ | 70% | $2 \times 10^5$ | 0.7 |
| Bound to Affi-FIXQ/S | 4.7 mg | $3.3 \times 10^8$ | 30% | $1.4 \times 10^8$ | 502 |
| Affinity-purified carboxylase | .402 mg | $3.88 \times 10^8$ | 34% | $1.93 \times 10^9$ | 7,000 |

We have affinity purified the carboxylase to 80-90% purity with a yield of 34%. The procedure is rapid and efficient. The entire purification can be accomplished in four days. It is difficult to compare different purification schemes, but by comparing final specific activities, it appears that our purification results in a carboxylase preparation that is 185-fold higher in specific activity than the best previously published method. From $^{14}CO_2$ incorporation into the pentapeptide FLEEL, we estimate the specific activity of our carboxylase prepared by Affi-FIXQ/S chromatography eluted by method II (FIG. 5) as $2.4 \times 10^9$ cpm/mg protein/hr. This represents a 7,000-fold purification. Hubbard et al. reported a specific activity of $1.3 \times 10^7$ cpm/mg protein/hr with a 107-fold purification from their affinity purification step. The results should be comparable, because the $CO_2$ used in the two experiments had the same specific activities.

carboxylase from a 25-ml Affi-FIXQ/S column, with a final yield of 34% of the starting activity. Glycerol, which is often used to stabilize the membrane protein during purification, proved to be an important stabilizer for carboxylase. It increases the thermal stability of carboxylase and also increases the half life of carboxylase at 4° C. Although 20% glycerol does not inhibit carboxylase binding to Affi-FIXQ/S, it does prevent carboxylase from being eluted by proFIX19 and also inhibits the enzyme activity. The purified carboxylase is very stable and can be stored at −70° C. for months without loss of activity.

EXAMPLE 2

Partial Sequencing of Carboxylase Enzyme

Carboxylase enzyme prepared by the two-step purification procedure set forth in Example 1 above was further purified by removing lipid by hexane/isopropanol extraction. The enzyme was then reconcentrated and separated on a preparative reducing SDS-PAGE. After electrophoresis, total proteins were transferred onto a nitrocellulose membrane by standard Western blot methodology. The transferred proteins were stained with Ponceau S to locate the carboxylase band, which was then cut out for amino acid sequencing. The amino acid sequencing was performed by Dr. William S. Lane, Harvard Microchem, Harvard University. Amino acid sequence was obtained from several tryptic peptides of the carboxylase. The seqence of the longest peptide, NT77, is given by SEQ ID NO:2. NT77 was 37 amino acids long. The sequence of a second peptide, NT56, is given by SEQ ID NO:3. The sequence of a third peptide, NT49 is given in SEQ ID NO:4. NT56 and NT49 were 12 and 16 amino acids long, respectively.

EXAMPLE 3

Preparation of Sequence

The codons for the amino acid sequence represented by SEQ ID NO:2 above were used to design several redundant oligonucleotides for use in the polymerase chain reaction (PCR). A mixture of 1024 oligonucleotides (SEQ ID NO:5) was synthesized to take into account the redundancy in the codons at the carboxy terminus of the 38 amino acid tryptic peptide NT77 given as SEQ ID NO:2; this mixture was used to synthesize the first strand cDNA with reverse transcriptase.

Two degenerate oligonucleotides were synthesized as PCR primers and used for the polymerase chain reaction. Oligonucleotides contained regular bases or contain 5-fluorouridine in order to reduce redundancy and were synthesized by Oligos Etc., Inc., Suite 266, 800 Village Walk, Guilford, Conn. 06457 USA. One of the oligonucleotide primers had the sequence: AAN NTN GCN TTN GGN MG (SEQ ID NO:6), where the N at residue 3 represents 5-fluorodeoxyuridine (F); the N at residue 4 represents F; the N at residue 6 represents F or G; the N at residue 9 represents F or G; the N at residue 12 represents F; and the N at residue 15 represents A,T, G, or C. The other oligonucleotide primer had the sequence: TC NCC NGC NGG YTC RAA (SEQ ID NO:7), where the N at residue 3 represents F or G; the N at residue 6 represents F or G; and the N at residue 9 represents F or G.

The polymerase chain reaction was performed by standard procedures (94° C., 1 min; 58° C., 3 min; 72° C., 2 min; 25 cycles) using Taq polymerase purchased from Perkin Elmer Cetus (Part No. N801-0046) and a Cetus thermal cycler obtained from Cetus.

A product of 86 nucleotides was obtained from the polymerase chain reaction described above and sequenced. A 55 nucleotide probe complementary to the coding sequence of the PCR product was then synthesized; this probe is given as SEQ ID NO:8.

EXAMPLE 4

Preparation of Bovine cDNA Sequence

The 55-nucleotide probe represented by SEQ ID NO:8 was synthesized by Oligos Etc., Inc. This probe is labelled with $^{32}P$ at the 5' terminus in accordance with known techniques and is used to screen a bovine cDNA library purchased from Stratagene, Inc. A Positive clone is obtained and identified as λZAP-CARB1.6. The positive clone is partially sequenced, and portions of the clone sequence are given as SEQ ID NO:9, SEQ ID NO:11, and SEQ ID NO:13. The peptides coded for by these sequences are given separately as SEQ ID NO:10, SEQ ID NO:12, and SEQ ID NO:14, respectively. Note that, in SEQ ID NO:10, amino acid residues 58 to 68 correspond to amino acid residues 1-11 of the tryptic peptide NT77 given as SEQ ID NO:2; in SEQ ID NO:10, amino acid residues 1-12 correspond to amino acid residues 1-12 of the tryptic peptide NT56 given as SEQ ID NO:3; in SEQ ID NO:12, amino acid residues 1-10 correspond to amino acid residues 28-37 of tryptic peptide NT77 given in SEQ ID NO:2; and in SEQ ID NO:14, amino acid residues 1-14 correspond to amino acid residues 1-14 of tryptic peptide NT49 given as SEQ ID NO:4.

The bacteriophage λZAP-CARB1.6 was deposited with the American Type Culture Collection, 12301 Parklawn Drive, Rockville, Md. 20852 USA in accordance with the provisions of the Budapest Treaty on Apr. 23, 1991, and has been assigned ATCC Accession Number 75002.

EXAMPLE 5

Preparation and Expression of Human cDNA Sequence

The 1.6 Kb insert from λZAP-CARB1.6 is used to screen a human cDNA library to a detect human cDNA sequence encoding a vitamin K dependent carboxylase. Screening is carried out by a standard in situ hybridization assay, see J. Sambrook et al., Molecular Cloning, A Laboratory Manual (2d Ed. 1989), under conditions represented by a wash stringency of 0.3M NaCl, 0.03M sodium citrate, and 0.1% SDS at a temperature of 60° C. or 70° C. A number of positive clones are detected.

None of the foregoing clones coded for the entire sequence of the gamma glutamyl carboxylase. They were important, however, because they allowed us to compare liver carboxylase to the carboxylase of another tissue. We screened a second cDNA library made with mRNA from a human cell line (HEL human erythroleukemia). From the HEL library we obtained a clone, SEQ ID NO:15, which included the entire coding sequence of the human carboxylase and some upstream and downstream sequences. The cDNA codes for a protein of 758 amino acids (SEQ ID NO:16) whose molecular weight is 87,542 (excluding carbohydrates). This clone is the authentic carboxylase and possesses the entire coding sequence.

Conclusive evidence that the clone of SEQ ID NO:15 contains the authentic human carboxylase is from transient expression in human 293 kidney cells. As discussed below, microsomes from cells transfected with pCMV.hGC+, which is the expression vector pCMV5 (cytomegalovirus promoter) containing the cDNA of SEQ ID NO:15 exhibited a 9-35 fold increase in carboxylase activity compared to microsomes from mock infected cells. The expression vector pCMV5, see S. Andersson, J. Biol. Chem. 264, 8222-8229 (1989), was a gift of Dr. David Russell.

Figure 6:
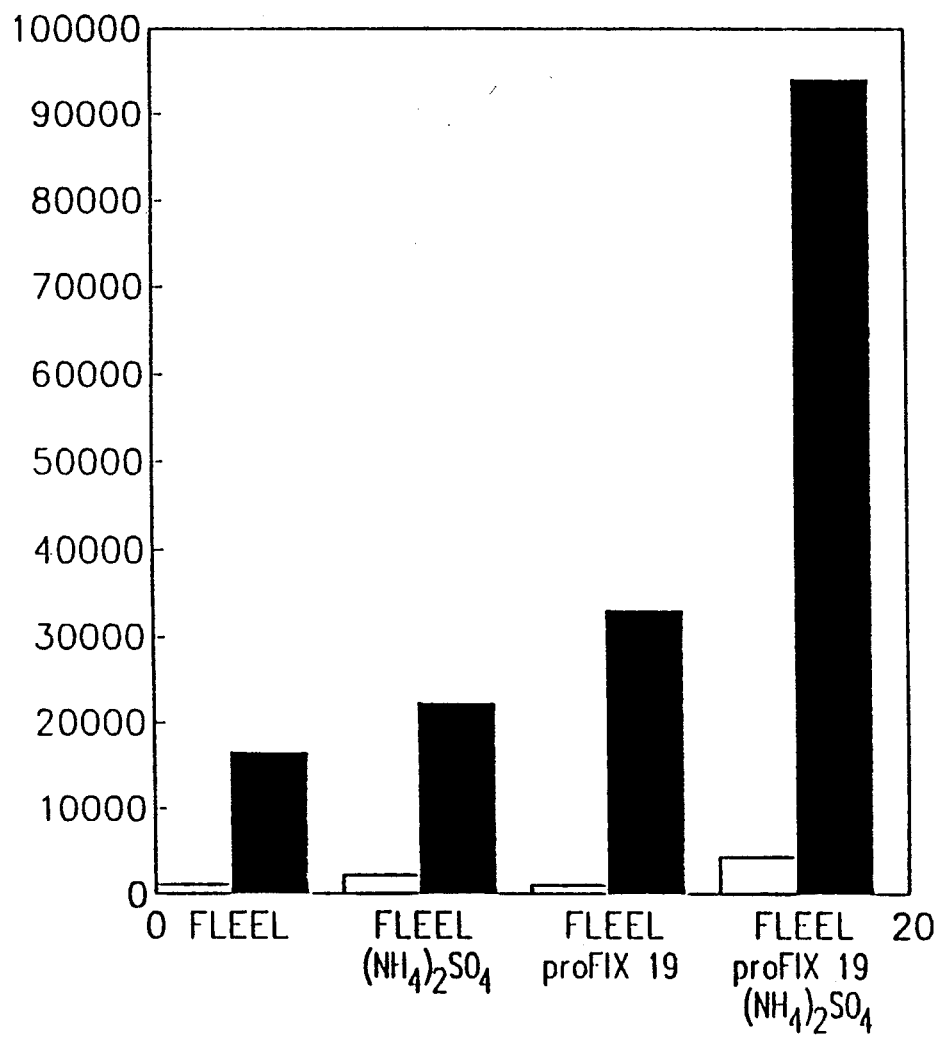
FIG. 6 shows transient expression of carboxylase in pCMV5 and pCMV.hGC+ transfected 293 cells.

FIG. 6 shows a comparison of transient expression of carboxylase in pCMV5 and pCMV.hGC+ transfected 293 cells. Purified plasmid DNA was used to transfect human kidney 293 cells with Calcium-Phosphate. See F. Graham and A. van der Eb, *Virology* 52 456-461 (1973). Forty-eight hours after transfection, cells from twenty 85-millimeter dishes were harvested to prepare microsomes according to known techniques. See, e.g., J. Girardot, *J. Biol. Chem.* 257, 15008-15011 (1982). Carboxylase activity was determined in accordance with known techniques (see, e.g., S-M. Wu et al., *Proc. Natl. Acad. Sci. USA* 88, 2236–2240 (1991), except that 0.16% phosphatidylcholine/0.32% CHAPS and 180 μg microsomal proteins from transient expression cells were used. The carboxylase activity of microsomes from mock infected cells (unfilled bars) and from cells transfected with pCMV.hGC+ (filled bars) are plotted pairwise. Each pair represents activity under different conditions of assay (indicated below the X axis). Carboxylase activity was quantitated by $^{14}CO_2$ incorporation into the synthetic peptide substrate FLEEL and is shown on the Y-axis in counts per minute.

*Escherichia coli* cells containing pCMV.hGC+, designated *E. coli*, pCMV.hGC+, was deposited with the American Type Culture Collection, 12301 Parklawn Drive, Rockville, Md. 20852 USA, in accordance with the provisions of the Budapest Treaty on Aug. 15, 1991, and has been assigned ATCC Accession Number 68666.

It is likely that the level of carboxylase can be increased greatly in stable cell lines. This can be done by standard amplification techniques and also by making the translation initiation region conform to the ideal (D. Cavener and S. Ray, Nucleic Acids Res. 19, 3185 (1991)).

It should be noted that the human carboxylase and bovine carboxylase, over the region where both sequences are known (664 amino acids) are 91% identical. The amino acid sequence of the liver and HEL carboxylase are also identical over the region where both sequences are available (354 amino acids). There are two differences in nucleotide sequence in the two human clones but they result in the same amino acid sequence. It is likely that some polymorphism will exist.

The foregoing examples are illustrative of the present invention, and are not to be taken as limiting thereof. The invention is defined by the following claims, with equivalents of the claims to be included therein.

---

That which is claimed is:

1. Isolated DNA encoding a vitamin K dependent carboxylase selected from the group consisting of:
   (a) isolated DNA selected from the group consisting of DNA which encodes bovine 94,000 dalton vitamin K dependent carboxylase and comprises the sequence of SEQ ID NO: 9, SEQ ID NO:11 or SEQ ID NO:13, and DNA having the sequence given herein as SEQ ID NO:15 and which encodes human vitamin K dependent carboxylase;
   (b) isolated DNA which hybridizes to the complementary strand of isolated DNA of (a) above under stringent conditions represented by a wash stringency of 0.3M NaCl, 0.03M sodium citrate, and 0.1% SDS at 70° C. and which encodes a vitamin K dependent carboxylase at least 75% homologous to isolated DNA of (a) above; and
   (c) isolated DNA differing from the isolated DNAs of (a) and (b) above in nucleotide sequence due to the degeneracy of the genetic code, and which encodes a vitamin K dependent carboxylase.

2. Isolated DNA according to claim 1, which encodes a carboxylase which activates a vitamin K dependent protein selected from the group consisting of Factor VII, Factor IX, Factor X, Protein C, Protein S, and Prothrombin.

3. A recombinant DNA molecule comprising cloning vector DNA and a DNA according to claim 1.

4. A recombinant DNA molecule according to claim 3, wherein said vector DNA comprises a vector selected from the group consisting of plasmids, adenoviruses, and cytomegaloviruses.

5. A recombinant DNA molecule according to claim 3, wherein said vector DNA comprises a baculovirus vector.

6. A host cell containing a recombinant DNA molecule of claim 3 which expresses the encoded carboxylase.

7. A host cell according to claim 6, wherein said host cell is a mammalian cell.

8. A host cell according to claim 6, wherein said host cell is selected from the group consisting of baby hamster kidney cells, mouse cells, human embryo cells, and chinese hamster ovary cells.

9. A host cell according to claim 6, wherein said host cell is an insect cell.

10. A host cell according to claim 6, wherein said host cell expresses a vitamin K-dependent protein.

11. A host cell according to claim 6, wherein said host cell expresses a vitamin K-dependent protein comprising a blood coagulation protein.

12. A host cell according to claim 6, wherein said host cell expresses a vitamin K dependent protein selected from the group consisting of Factor VII, Factor IX, Factor X, Protein C, Protein S, and Prothrombin.

13. In a method of making a vitamin K dependent protein which comprises culturing a host cell which expresses a vitamin K dependent protein in the presence of vitamin K, and then harvesting said vitamin K dependent protein from the culture, the improvement comprising:
   employing as said host cell a eukaryotic host cell containing a recombinant DNA molecule comprising cloning vector DNA operable in said host cell and a DNA encoding a vitamin K dependent carboxylase selected from the group consisting of:
   (a) isolated DNA selected from the group consisting of DNA which encodes bovine 94,000 dalton vitamin K dependent carboxylase and comprises the sequence of SEQ ID NO: 9, SEQ ID NO:11 or SEQ ID NO:13, and DNA having the sequence given herein as SEQ ID NO:15 and which encodes human vitamin K dependent carboxylase;
   (b) isolated DNA which hybridizes to the complementary strand of isolated DNA of (a) above under stringent conditions represented by a wash stringent of 0.3M NaCl, 0.03M sodium citrate, and 0.1% SDS at 70° C. and which encodes a vitamin K dependent carboxylase at least 75% homologous to isolated DNA of (a) above; and
   (c) isolated DNA differing from the isolated DNAs of (a) and (b) above in nucleotide sequence due to the degeneracy of the genetic code, and which encodes a vitamin K dependent carboxylase;
   said host cell expressing increased amounts of said vitamin K dependent protein due to the expression of functional vitamin K dependent carboxylase by said host cell.

14. A method according to claim 13, wherein said vitamin K dependent protein comprises a blood coagulation protein.

15. A method according to claim 13, wherein said vitamin K dependent protein is selected from the group consisting of Factor VII, Factor IX, Factor X, Protein C, Protein S, and Prothrombin.

16. A method according to claim 13, wherein said vector DNA comprises a vector selected from the group consisting of plasmids, adenoviruses, and cytomegaloviruses.

17. A method according to claim 13, wherein said vector DNA comprises a baculovirus vector.

18. A method according to claim 13, wherein said host cell is a mammalian cell.

19. A method according to claim 13, wherein said host cell is an insect cell.

20. A method according to claim 13, wherein said vitamin K-dependent carboxylase is bovine vitamin K dependent carboxylase.

21. Isolated and purified vitamin K dependent carboxylase, which carboxylase is coded for by DNA selected from the group consisting of:
(a) isolated DNA selected from the group consisting of DNA which encodes bovine 94,000 dalton vitamin K dependent carboxylase and comprises the sequence of SEQ ID NO: 9, SEQ ID NO:11 or SEQ ID NO:13, and DNA having the sequence given herein as SEQ ID NO:15 and which encodes human vitamin K dependent carboxylase;
(b) isolated DNA which hybridizes to the complementary strand of isolated DNA of (a) above under stringent conditions represented by a wash stringency of 0.3M NaCl, 0.03M sodium citrate, and 0.1% SDS at 70° C. and which encodes a vitamin K dependent carboxylase at least 75% homologous to isolated DNA of (a) above; and
(c) isolated DNA differing from the isolated DNAs of (a) and (b) above in nucleotide sequence due to the degeneracy of the genetic code, and which encodes a vitamin K dependent carboxylase.

22. Isolated DNA encoding mammalian vitamin K dependent carboxylase selected from the group consisting of:
(a) isolated DNA selected from the group consisting of DNA which encodes bovine 94,000 dalton vitamin K dependent carboxylase and comprises the sequence of SEQ ID NO: 9, SEQ ID NO:11 or SEQ ID NO:13, and DNA having the sequence given herein as SEQ ID NO:15 and which encodes human vitamin K dependent carboxylase;
(b) isolated mammalian DNA which hybridizes to the complementary strand of isolated DNA of (a) above under stringent conditions represented by a wash stringency of 0.3M NaCl, 0.03M sodium citrate, and 0.1% SDS at 70° C. and which encodes a vitamin K dependent carboxylase at least 75% homologous to isolated DNA of (a) above; and
(c) isolated DNA differing from the isolated DNAs of (a) and (b) above in nucleotide sequence due to the degeneracy of the genetic code, and which encodes a vitamin K dependent carboxylase.

23. Isolated DNA according to claim 22, which encodes a carboxylase which activates a vitamin K dependent protein selected from the group consisting of Factor VII, Factor IX, Factor X, Protein C, Protein S, and Prothrombin.

24. A recombinant DNA molecule comprising cloning vector DNA and a DNA according to claim 22.

25. A recombinant DNA molecule according to claim 24, wherein said vector DNA comprises a vector selected from the group consisting of plasmids, adenoviruses, and cytomegaloviruses.

26. A recombinant DNA molecule according to claim 24, wherein said vector DNA comprises a baculovirus vector.

27. A host cell containing a recombinant DNA molecule of claim 24 which expresses the encoded carboxylase.

28. A host cell according to claim 27, wherein said host cell is a mammalian cell.

29. A host cell according to claim 27, wherein said host cell is selected from the group consisting of baby hamster kidney cells, mouse cells, human embryo cells, and chinese hamster ovary cells.

30. A host cell according to claim 27, wherein said host cell is an insect cell.

31. A host cell according to claim 27, wherein said host cell expresses a vitamin K-dependent protein.

32. A host cell according to claim 27, wherein said host cell expresses a vitamin K-dependent protein comprising a blood coagulation protein.

33. A host cell according to claim 27, wherein said host cell expresses a vitamin K dependent protein selected from the group consisting of Factor VII, Factor IX, Factor X, Protein C, Protein S, and Prothrombin.

34. In a method of making a vitamin K dependent protein which comprises culturing a host cell which expresses a vitamin K dependent protein in the presence of vitamin K, and then harvesting said vitamin K dependent protein from the culture, the improvement comprising:
employing as said host cell a eukaryotic host cell containing a recombinant DNA molecule comprising cloning vector DNA operable in said host cell and DNA encoding mammalian vitamin K dependent carboxylase selected from the group consisting of:
(a) isolated DNA selected from the group consisting of DNA which encodes bovine 94,000 dalton vitamin K dependent carboxylase and comprises the sequence of SEQ ID NO: 9, SEQ ID NO:11 or SEQ ID NO:13, and DNA having the sequence given herein as SEQ ID NO:15 and which encodes human vitamin K dependent carboxylase;
(b) isolated mammalian DNA which hybridizes to the complementary strand of isolated DNA of (a) above under stringent conditions represented by a wash stringency of 0.3M NaCl, 0.03M sodium citrate, and 0.1% SDS at 70° C. and which encodes a vitamin K dependent carboxylase at least 75% homologous to isolated DNA of (a) above; and
(c) isolated DNA differing from the isolated DNAs of (a) and (b) above in nucleotide sequence due to the degeneracy of the genetic code, and which encodes a vitamin K dependent carboxylase;
said host cell expressing increased amounts of said vitamin K dependent protein due to the expression of functional vitamin K dependent carboxylase by said host cell.

35. A method according to claim 34, wherein said vitamin K dependent protein comprises a blood coagulation protein.

36. A method according to claim 34, wherein said vitamin K dependent protein is selected from the group consisting of Factor VII, Factor IX, Factor X, Protein C, Protein S, and Prothrombin.

37. A method according to claim 34, wherein said vector DNA comprises a vector selected from the group consisting of plasmids, adenoviruses, and cytomegaloviruses.

38. A method according to claim 34, wherein said vector DNA comprises a baculovirus vector.

39. A method according to claim 34, wherein said host cell is a mammalian cell.

40. A method according to claim 34, wherein said host cell is an insect cell.

41. A method according to claim 34, wherein said vitamin K-dependent carboxylase is bovine vitamin K dependent carboxylase.

42. Isolated and purified mammalian vitamin K dependent carboxylase, which carboxylase is coded for by DNA selected from the group consisting of:
   (a) isolated DNA selected from the group consisting of DNA which encodes bovine 94,000 dalton vitamin K dependent carboxylase and comprises the sequence of SEQ ID NO: 9, SEQ ID NO:11 or SEQ ID NO13, and DNA having the sequence given herein as SEQ ID NO:15 and which encodes human vitamin K dependent carboxylase;
   (b) isolated mammalian DNA which hybridizes to the complementary strand of isolated DNA of (a) above under stringent conditions represented by a wash stringency of 0.3M NaCl, 0.03M sodium citrate, and 0.1% SDS at 70° C. and which encodes a vitamin K dependent carboxylase at least 75% homologous to isolated DNA of (a) above; and
   (c) isolated DNA differing from the isolated DNAs of (a) and (b) above in nucleotide sequence due to the degeneracy of the genetic code, and which encodes a vitamin K dependent carboxylase.

43. Isolated DNA encoding mammalian vitamin K dependent carboxylase selected from the group consisting of:
   (a) isolated DNA selected from the group consisting of DNA encoding bovine 94,000 dalton vitamin K-dependent carboxylase which bovine carboxylase comprises the sequence given in SEQ ID NO: 2, 3, 4, 10, 12, or 14 and DNA encoding human vitamin K dependent carboxylase, which human vitamin K dependent carboxylase has the sequence given herein as SEQ ID NO:16.

44. Isolated DNA according to claim 43 having the sequence given herein as SEQ ID NO:15.

45. A recombinant DNA molecule comprising cloning vector DNA and a DNA according to claim 43.

46. A host cell containing a recombinant DNA molecule of claim 45 which expresses the encoded vitamin K dependent carboxylase.

47. A host cell according to claim 46, wherein said host cell is a mammalian cell.

48. A host cell according to claim 46, wherein said host cell is an insect cell.

49. A host cell according to claim 46, wherein said host cell expresses a vitamin K-dependent protein.

50. A host cell according to claim 46, wherein said host cell expresses a vitamin K-dependent protein comprising a blood coagulation protein.

51. Isolated DNA encoding a human vitamin K dependent carboxylase selected from the group consisting of:
   (a) isolated DNA having the sequence given herein as SEQ ID NO:15 and which encodes human vitamin K dependent carboxylase;
   (b) isolated DNA which hybridizes to isolated DNA of (a) above under conditions represented by a wash stringency of 0.3M NaCl, 0.03M sodium citrate, and 0.1% SDS at 60° C. and which encodes a vitamin K dependent carboxylase at least 75% homologous to isolated DNA of (a) above; and
   (c) isolated DNA differing from the isolated DNAs of (a) and (b) above in nucleotide sequence due to the degeneracy of the genetic code, and which encodes a vitamin K dependent carboxylase;
which isolated DNA encodes human vitamin K dependent carboxylase.

52. A recombinant DNA molecule comprising cloning vector DNA and a DNA according to claim 51.

53. A recombinant DNA molecule according to claim 52, wherein said vector DNA comprises a vector selected from the group consisting of plasmids, adenoviruses, and cytomegaloviruses.

54. A recombinant DNA molecule according to claim 52, wherein said vector DNA comprises a baculovirus vector.

55. A host cell containing a recombinant DNA molecule of claim 52 which expresses the encoded carboxylase.

56. A host cell according to claim 55, wherein said host cell is a mammalian cell.

57. A host cell according to claim 55, wherein said host cell is an insect cell.

58. A host cell according to claim 6, 27, 46, or 55, wherein said host cell is yeast cell.

59. A method according to claim 13 or 34, wherein said host cell is a yeast cell.

60. A method according to claim 13 or 34, wherein said DNA encoding a vitamin K dependent carboxylase encodes human vitamin K dependent carboxylase.

* * * * *

UNITED STATES PATENT AND TRADEMARK OFFICE
CERTIFICATE OF CORRECTION

PATENT NO. : 5,268,275

DATED : 07 December 1993

INVENTOR(S) : Darrel W. Stafford and Sheue-Mei Wu

It is certified that error appears in the above-identified patent and that said Letters Patent is hereby corrected as shown below:

Column 12, Lines 1 & 2, "NaH1-4CO$_3$" to read --NaH$^{14}$CO$_3$--.

Column 34, Line 57, correct "stringent" to read --stringency--.

Signed and Sealed this

Third Day of May, 1994

Attest:

BRUCE LEHMAN

Attesting Officer

Commissioner of Patents and Trademarks